US008071375B2

(12) United States Patent
Clark et al.

(10) Patent No.: US 8,071,375 B2
(45) Date of Patent: Dec. 6, 2011

(54) USE OF IL-6-TYPE CYTOKINES FOR MATURATION OF OOCYTES

(75) Inventors: Ann M. Clark, Weymouth, MA (US); Daniel Gustavo de Matos, Pembroke, MA (US); Jennifer A. Jackson, Pembroke, MA (US); Stephen S. Palmer, Plympton, MA (US); Cam Anh T. Tran, Quincy, MA (US)

(73) Assignee: Merck Serono SA, Coinsins, Vaud (CH)

( * ) Notice: Subject to any disclaimer, the term of this patent is extended or adjusted under 35 U.S.C. 154(b) by 408 days.

(21) Appl. No.: 10/998,080

(22) Filed: Nov. 26, 2004

(65) Prior Publication Data

US 2005/0142107 A1 Jun. 30, 2005

Related U.S. Application Data

(60) Provisional application No. 60/525,279, filed on Nov. 26, 2003.

(51) Int. Cl.
*C12N 5/075* (2010.01)
*A61K 38/20* (2006.01)
*C07K 14/54* (2006.01)

(52) U.S. Cl. ........ 435/377; 435/375; 435/384; 435/386; 530/351

(58) Field of Classification Search .................... None
See application file for complete search history.

(56) References Cited

U.S. PATENT DOCUMENTS

| 4,554,101 A | 11/1985 | Hopp |
| 6,274,135 B1 * | 8/2001 | Keith et al. ................. 424/85.2 |
| 2001/0028878 A1 * | 10/2001 | Lindenberg et al. ......... 424/93.7 |

FOREIGN PATENT DOCUMENTS

WO  WO 97/30146  8/1997

OTHER PUBLICATIONS

E. Nilsson et al., "Leukemia inhibitory factor (LIF) induces the primordial to primary follicle transitionin rat ovaries", Mol. Cel. Endocrinol. 188:65-75, Feb. 25, 2002.*
P. R. Kezele et al., "Insulin but not insulin-like growth factor-1 promotes the primordial to primary follicle transition", Mol. Cell. . Endocrinol. 192:37-43, 2002 (Feb. 28, 2003).*
C. Huyser et al., "Interleukine-1beta, Interleukin-6, and Growth Hormone Levels in Human Follicular Fluid", J. Assisted Reprod. and Genet., 11(4):193-202, 1994.*
T. Taga; "gp130 and the Interleukin-6 Family of Cytokines". Annual Review of Immunology vol. 15: 797-819 (Volume publication date Apr. 1997).*
N. Garrido et al., Follicular hormonal environment and embryo quality in women with endometriosis, Human Reproduction Update 2000, vol. 6 No. 1 pp. 67-74.*
http://www.pdrel.com/View/StedmanSearch/DocumentRetrive. aspx?documentld=9628, accessed Sep. 20, 2010, definition of "cumulus".*
http://www.pdrel.com/View/StedmanSearch/DocumentRetrive. aspx?documentld=02783, accessed Sep. 20, 2010, defnition of "Antrum".*
Endotext.com,(http://www.endotext.org/female/female1/femaleframe1.htm) , paragraph on oocyte-granulosa cell connections, accessed Sep. 20, 2010.*
Abe, T., et al., "Macrophage Differentiation Inducing Factor from Human Monocytic Cells Is Equivalent to Murine Leukemia Inhibitory Factor," The Journal of Biological Chemistry, vol. 264, No. 15, pp. 8941-8945 (1989).
Baumann, H., et al., "Hepatocyte-Stimulating Factor III Shares Structural and Functional Identity with Leukemia-Inhibitory Factor," The Journal of Immunology, vol. 143, No. 4, pp. 1163-1167 (1989).
Eckert, J., "mRNA Expression of Leukaemia Inhibitory Factor (LIF) and its Receptor Subunits Glycoprotein 130 and LIF-Receptor-13 in Bovine Embryos Derived in vitro or in vivo," Molecular Human Reproduction, vol. 4, No. 10, pp. 957-967 (1998).
International Search Report dated Apr. 22, 2005 for PCT/US2004/039757.
Kawasaki, F., et al., "The Clinical Role of Interleukin-6 and Interleukin-6 Soluble Receptor in Human Follicular Fluids," Clin. Exp. Ed., vol. 3, pp. 27-31 (2003).
Koopman, P., et al., "A Factor Produced by Feeder Cells Which Inhibits Embryonal Carcinoma Cell Differentiation," Experimental Cell Research, vol. 154, pp. 233-242 (1984).
Kyte, J., et al., "A Simple Method for Displaying the Hydropathic Character of a Protein," Journal of Molecular Biology, vol. 157, pp. 105-132 (1982).
Moreau, J., et al., "Leukaemia Inhibitory Factor is Identical to the Myeloid Growth Factor Human Interleukin for DA cells," Nature, vol. 336, pp. 690-692 (1988).
Mori, M., et al., "Purification of a Lipoprotein Lipase-Inhibiting Protein Produced by a Melanoma Cell Line Associated with Cancer Cachexia," Biochemical and Biophysical Research Communications, vol. 160, No. 3, pp. 1085-1092 (1989).
Pennica, D., et al., "Biological Activities and Binding to the Leukemia Inhibitory Factor Receptor/gp130 Signaling Complex," The Journal of Biological Chemistry, vol. 270, No. 18, pp. 10915-10922 (1995).
Picton, H., et al., "Growth and Maturation of Oocytes in vitro," Reproduction Supplement, vol. 61, pp. 445-462 (2003).
Smith, A., et al., "Buffalo Rat Liver Cells Produce a Diffusible Activity Which Inhibits the Differentiation of Murine Embryonal Carcinoma and Embryonic Stem Cells," Developmental Biology, vol. 121, pp. 1-9 (1987).
Sutton, M., "Effects of in-vivo and in-vitro Environments on the Metabolism of the Cumulus-Oocyte Complex and its Influence on Oocyte Developmental Capacity," Human Reproduction Update, vol. 9, No. 1, pp. 35-48 (2003).

(Continued)

*Primary Examiner* — Lorraine Spector
(74) *Attorney, Agent, or Firm* — Morgan Lewis & Bockius LLP

(57) ABSTRACT

The use of certain IL-6-type cytokines for the in vitro maturation of mammalian oocytes is described. The in vitro matured oocytes may be used in in vitro fertilization protocols.

11 Claims, 18 Drawing Sheets

OTHER PUBLICATIONS

Tomida, M., et al., "Purification of a Factor Inducing Differentiation of Mouse Myeloid Leukemic M1 Cells from Conditioned Medium of Mouse Fibroblast L929 Cells," The Journal of Biological Chemistry, vol. 259, No. 17, pp. 10978-10982 (1984).

Yamamori, T., et al., "The Cholinergic Neuronal Differentiation Factor from Heart Cells Is Identical to Leukemia Inhibitory Factor," Science, vol. 246, pp. 1412-1416 (1989).

Zolti, M., et al., "Cytokine Involvement in Oocytes and Early Embryos," Fertility and Sterility, vol. 56, No. 2, (1991).

Liu, Zhilin, et al., "Interleukin-6: an Autocrine Regulator of the Mouse Cumulus Cell-Oocyte Complex Expansion Process," Endocrinology, vol. 150, No. 7, pp. 3360-3368 (Jul. 2009).

Diamond, M., et al., "Human Follicular Fluid Insulin Concentrations," Journal of Clinical Endocrinology & Metabolism, vol. 61, No. 5, pp. 990-992 (1985).

* cited by examiner n=2 (independent replicates) (Mean ± SE mean)

n=2 (independent replicates) (Mean ± SE mean)

FIGURE 17

Embryo Transfer: Birth Rates

| Treatments | Total Birth rate (%) | Live birth rate (%) | Stillbirth rate (%) | Pregnancy rate (%) |
|---|---|---|---|---|
| In Vivo Matured Control (ovulated oocytes) | 26/137 (19) | 23/137 (17) | 3/137 (2) | 11/14 (79) |
| FSH (0.2 IU/ml) | 7/56 (12) | 5/56 (9) | 2/56 (4) | 4/6 (67) |
| FSH + 1000 ng/ml LIF | 18/76 (24) | 15/76 (20) | 3/76 (4) | 7/8 (87) |
| FSH + 1 ng/ml LIF | 8/67 (12) | 8/67 (12) | 0 | 4/7 (57) |
| FSH + 0.1 ng/ml LIF | 6/59 (10) | 6/59 (10) | 0 | 4/6 (67) |
| ---- + 1000 ng/ml LIF | 4/59 (7) | 3/59 (5) | 1/59 (2) | 3/7 (43) |
| ---- +   1 ng/ml LIF | 10/64 (16) | 9/64 (14) | 1/64 (2) | 6/8 (75) |

Total Birth rate (%): Total pups/total blastocyst transferred (Percentage)
Live Birth rate (%): Live pups/total blastocyst transferred (Percentage)
Stillbirth rate (%): Dead pups/total blastocyst transferred (Percentage)
Pregnancy rate (%): Females pregnant/total female transferred (Percentage)

n=4
(4 replicates of the same experiment)

n=2 (independent replicates) (Mean ± SE mean)

USE OF IL-6-TYPE CYTOKINES FOR MATURATION OF OOCYTES

CROSS REFERENCE TO RELATED APPLICATIONS

This application claims the benefit of U.S. Provisional Application No. 60/525,279, filed Nov. 26, 2003.

BACKGROUND OF THE INVENTION

1. Field of the Invention

The present invention relates to methods of in vitro maturation of mammalian oocytes.

2. Description of Related Art a. Ovary

The mammalian ovary is responsible for the production of mature oocytes from germ cells and the production of hormones that permit the development of secondary sexual characteristics and the successful completion of pregnancy. The ovary is roughly divided into an outer cortex and an inner, vascular medulla. The stroma of the ovary spans both the cortex, which contains the ovarian follicles in various stages of development, and medulla regions.

A mature follicle is a highly complex unit having certain distinct cell types and consists of several layers of somatic cells surrounding a fluid-filled cavity "antrum" in which resides a single oocyte bathed by follicular fluid. The follicle provides the nutrients and regulatory signals required for oocyte growth and maturation.

Oocytes present in the adult ovary develop from a definite number of primordial germ cells (PGC) that migrate from extragonadal sites to the gonadal ridge to form the primitive ovary during fetal development. Once established in the developing ovary, the proliferating PGC begin to differentiate into oogonia, which are the stem cells that give rise to all the oocytes in the ovary. The population of oogonia goes through a predetermined, species-specific number of mitotic cycles until the cells enter the prophase of meiosis and become oocytes. Meiosis becomes arrested at the diplotene stage of prophase and remains at that stage until folliculogenesis begins at puberty. The meiosis-arrested primary oocytes are contained within a primordial follicle.

b. Primordial Follicles

Primordial follicles are the fundamental developmental units of the mammalian ovary. The number of primordial follicles is determined during early life and most of them remain in a resting state. The store of primordial follicles is not renewable and serves the entire reproductive life span of the adult. Before and throughout the reproductive life of the female, a number of these primordial follicles leave the resting state and start to grow (initial recruitment). The follicles develop to the antral stage where most undergo atresia; however, some of these follicles are rescued (cyclic recruitment) to reach the preovulatory stage. The end of normal reproductive life tyically occurs when the pool of resting primordial follicles is exhausted.

c. Folliculogenesis

Folliculogenesis is the process responsible for the development of ovulatory follicles and the release of one or more mature oocytes at a fixed interval throughout the reproductive life of a female. Folliculogenesis is resumed after a long quiescent phase and involves sequential subcellular and molecular transformations by various components of the follicle. During postnatal life, ovarian follicles continue to grow, mature and either ovulate or regress. Follicles are recruited continuously until the original store is exhausted.

Primordial follicles are activated to become primary follicles. Although oocytes from primordial and primary follicles are not significantly different in size, important changes take place during the primary follicle stage. The corona radiata develops gap junctions with the oocyte and the zona pellucida begins to form between the two cell types. The zona pellucida will not completely surround the oocyte until the follicle reaches the late preantral stage. Secondary follicles begin to appear when the follicular cells of the primary follicles undergo intensive mitotic division. A secondary follicle contains at least two layers of granulosa cells with the theca cells identifiable outside the basement membrane and the follicle contains a fine capillary network. Tertiary or antral follicles are characterized by the presence of a cavity known as antrum, which is filled with follicular fluid. The first antral follicles have an extensive network of gap junctions that permits the transfer of nutrients and regulatory signals between the oocyte and the granulosa cells. Antral follicles develop until they reach the preovulatory size. Inside the antral follicle, cumulus cells surround the oocyte. In vivo, expansion of the cumulus-oocyte complex (COC) is induced after the LH surge at the endpoint of ovulation in preparation for fertilization of the oocyte.

d. Oocyte Maturation

Oocyte maturation is a complex phenomenon during which the oocyte progresses from the diplotene to the metaphase II stage (nuclear maturation) in response to the ovulatory LH surge. Once reaching the metaphase II stage, the oocyte remains arrested until fertilization takes place and the oocyte completes meiosis and forms the pronucleus. Oocyte maturation also involves transformations at the cytoplasmic level that prepare the cell to support fertilization and early embryonic development (cytoplasmic maturation). The final steps of oocyte maturation are crucial to the acquisition of functional properties necessary for further development.

e. In Vitro Fertilization

In vitro fertilization (IVF) of human oocytes is a widely practiced medical technique used to overcome various forms of female and male infertility thereby opening a vast new frontier of research and treatment for the infertile couples. Despite the success of IVF, there is a significant need for improved methods of infertility treatment because about one out of five couples are unable to achieve a successful pregnancy using current IVF treatments.

When IVF was first performed, one mature unfertilized oocyte was removed from the ovary just prior to ovulation. The mature oocyte was fertilized in a laboratory dish (in vitro) and the resulting embryo was transferred back to the woman's uterus. However, it was found that if more oocytes were available for fertilization, there were more embryos available for transfer to the uterus and this significantly increased the pregnancy rate. Therefore, the current clinical practice involves giving patients hormone injections in order to induce the maturation of approximately twenty oocytes.

The standard IVF treatment includes a long phase of hormone stimulation of the female patient, e.g. 30 days, which is initiated by administering a gonadotropin releasing hormone (GnRH) agonist or antagonist to suppress the patient's own follicle stimulating hormone (FSH) and luteinizing hormone (LH). This is followed by injections of exogenous gonadotropins, e.g. FSH and/or LH, in order to ensure development of multiple preovulatory follicles. Just prior to ovulation, multiple in vivo-matured oocytes are removed from the ovaries. The isolated mature oocytes are subsequently fertilized in vitro and cultured, typically for three to six days, before transferring the developed embryos back into the uterus at the 4-8 cell stage.

Continuous efforts have been made to optimize and simplify IVF procedures in order to improve the current overall pregnancy rate of about 25% to 35%. Due to the low pregnancy rates, it is common to transfer two to five embryos in an attempt to increase pregnancy rates.

The administration of hormone injections to induce the maturation of many oocytes simultaneously is known as controlled ovarian hyperstimulation (COH). The advantage of COH is the availability of many more mature oocytes for fertilization, which increases the chances of pregnancy. However, the woman undergoing COH must be closely monitored by daily ultrasound examinations of the ovaries and blood hormone measurements because excessive ovarian stimulation may cause ovarian hyperstimulation syndrome (OHSS), which is a serious and potentially fatal condition. COH is not effective for a number of females, including some with polycistic ovary disease.

f. In Vitro Maturation of Oocytes

The side effects associated with COH could be avoided if immature oocytes could be removed from the oocytes and matured in vitro. Mammalian oocytes undergo spontaneous maturation upon removal from the follicle. Although oocytes matured in vitro have rates of nuclear maturation, fertilization and cleavage similar to in vivo matured oocytes, in vitro matured oocytes have significantly lower blastocyst rates and developmental potential.

Early in each menstrual cycle, several oocytes begin to grow in preparation for undergoing maturation and becoming developmentally competent, i.e., competent to be fertilized and develop into a healthy fetus. By approximately the fifth to seventh day of the cycle, one oocyte becomes dominant and continues to grow while the other oocytes are induced to degenerate. Once an oocyte becomes dominant, it grows and undergoes metabolic changes for approximately one week prior to becoming mature at the time of ovulation. Oocytes that do not undergo this growth phase will mature in vitro and can be fertilized, but are less likely to be developmentally competent. Therefore, the optimal time to obtain the largest number of immature oocytes is early in the cycle before any oocytes have begun to degenerate. However, oocytes removed early in the menstrual cycle and matured in vitro, are less likely to be developmentally competent.

Numerous events within the antral follicle affect oocyte maturation and the acquisition of developmental competency, including: (i) interactions between somatic cells of the follicle (in particular cumulus cells) and the oocyte; (ii) the composition of follicular fluid; and (iii) the temperature and vascularity of the follicular environment. Many of these factors change with follicle size and oocyte growth. In contrast, culture conditions for IVM are based on somatic cells that often do not reflect the follicular environment, and/or have complex compositions or additives such as macromolecule supplements that are undefined in nature. Metabolites typically included in IVM media such as glucose, pyruvate, oxygen and amino acids have been shown to have differential influences on oocyte maturation and competency. Manipulation of these factors and application of gained knowledge of the in vivo environment may result in improved in vitro oocyte maturation and overall in vitro embryo production.

g. IL-6-Type Cytokines

The IL (interleukin)-6-type cytokines, which include IL-6, IL-11, LIF (leukemia inhibitory factor), OSM (oncostatin M), CNTF (ciliary neurotrophic factor), CT-1 (cardiotrophin-1) and CLC (cardiotrophin-like cytokine), activate target genes involved in differentiation, survival, apoptosis and proliferation. IL-6-type cytokines bind to plasma membrane receptor complexes containing the common signal transducing receptor chain gp 130 (glycoprotein 130). Signal transduction involves the activation of JAK (Janus kinase) tyrosine kinase family members, leading to the activation of transcription factors of the STAT (signal transducers and activators of transcription) family. Another major signaling pathway for IL-6-type cytokines is the MAPK (mitogen-activated protein kinase) cascade.

Receptors involved in recognition of the IL-6-type cytokines can be subdivided into the non-signalling $\alpha$-receptors and the signal transducing receptors. The non-signalling $\alpha$-receptors include, but are not limited to, IL-6R$\alpha$, IL-11R$\alpha$, and CNTFR$\alpha$, where R refers to receptor. The signal transducing receptors include, but are not limited to, gp130, LIFR, and OSMR. The signal transducing receptors associate with JAKs and become tyrosine phosphorylated in response to cytokine stimulation. Each of the IL-6-type cytokines is characterized by a certain profile of receptor recruitment that in all cases involves at least one molecule of gp130.

IL-6, IL-11 and CNTF first bind specifically to their respective $\alpha$-receptor subunits. Here, only the complex of cytokine and $\alpha$-receptor efficiently recruits the signalling receptor subunits. IL-6 and IL-11 signal via gp130 homodimers. Most other IL-6 type cytokines signal via heterodimers of either gp130 and the LIFR (LIF, CNTF, CT-1 and CLC) or gp130 and the OSMR (OSM). OSM is able to recruit two different receptor complexes: both LIFR-gp130 and OSMR-gp130 heterodimers. LIF and OSM directly engage their signalling receptor subunits without requirement for additional $\alpha$-receptor subunits.

1) LIF

LIF elicits a diversity of biological effects on many cell types, including embryonic stem cells, primordial germ cells, neurons, adipocytes, hepatocytes, and osteoblasts. LIF affects various endocrine cell types (utero-placenta unit, bone metabolism, adrenal, ovarian, and testicular). The diversity in biological activity is reflected in the various synonyms of LIF, which include hepatocyte stimulating factor III (HSF III; Baumann and Wong, J. Immunol. 143: 1163, 1989); cholinergic nerve differentiation factor (CNDF; Yamamori et al., Science 246: 1412, 1990); melanoma-derived lipoprotein lipase inhibitor (MLPLI; Mori et al., Biochem. Biophys Res. Comm. 160: 1085, 1989); human interleukin for DA cells (HILDA; Moreau et al., Nature 336: 690, 1988); differentiation factor (D-factor; Tomida et al., J. Biol. Chem. 259: 10978, 1984); differentiation inhibitory factor (DIF; Abe et al., J. Biol. Chem. 264: 8941, 1989); differentiation inhibitory activity (DIA; Smith and Hooper, Devel. Biol. 121: 1, 1987); and differentiation retarding factor (DRF; Koopman and Cotton, Exp. Cell. Res. 154: 233, 1984).

LIF plays a central role in the regulation of diverse adult and embryonic systems. In the reproductive systems, LIF is an important cytokine in early pregnancy. Indeed, female LIF knockout mice are infertile because of a defect in the process of embryonic implantation. LIF is present in human follicular fluid and its levels are regulated according to the stage of antral follicle development. LIF levels in follicular fluid are also responsive to human chorionic gonadotropin (hCG). Cultured granulosa cells from mature follicles, but not from immature follicles, exhibit an increase in LIF production after treatment with $\beta$hCG ($\beta$-human CG), suggesting that LIF might be involved in ovulation and final oocyte development. Furthermore, LIF has been shown to promote the primordial to primary follicle transition in rats.

LIF is also an important factor in the in vitro culturing of embryonic stem (ES) cells and embryonic germ (EG) cells. EG cells or ES cells retain the stem cell phenotype in vitro when cultured on a feeder layer of fibroblasts when cultured in medium conditioned by certain cells or by the exogenous addition of LIF. In the absence of feeder cells, conditioned medium or exogenous LIF, ES or EG cells spontaneously differentiate into a wide variety of cell types.

2) CT-1

CT-1 causes hypertrophy of cardiac myocytes and has pleiotropic effects on various other cell types. Pennica et al. (J Biol. Chem. 1995 May 5; 270(18): 10915-22) disclose that CT-1 inhibited the differentiation of mouse embryonic stem cells. In vitro biological assays indicated that CT-1 was active in assays where LIF was active and vice-versa. These data showed that CT-1 had a wide range of hematopoietic, neuronal, and developmental activities and that it could act via the LIF receptor and the gp130 signalling subunit. Pennica et al. predict that CT-1 should mimic the many in vitro and in vivo effects of LIF.

WO9730146 discloses a method of enhancing the maintenance of pregnancy in a mammal by culturing an embryo in a medium containing CT-1 prior to introduction of the embryo into a mammal. WO9730146 suggests that media containing CT-1 may be suitable for early manipulative procedures on the oocyte/embryo such as in vitro fertilization, embryo splitting and nuclear transfer where survival rates of embryos are low.

3) OSM

Oncostatin M (OSM) is a pleiotropic cytokine produced late in the activation cycle of T-cells and macrophages that has been extensively characterized with numerous activities attributed to it. OSM was originally isolated from conditioned media of a phorbol ester-treated histiocytic lymphoma cell line, U937, based on the ability to inhibit the growth or development of a human melanoma cell line.

OSM binds to three cell surface receptors. OSM binds to a gp130 polypeptide, also known as the IL-6 signal transduction subunit, with a low affinity. In a second, intermediate affinity interaction, OSM and LIF compete for binding to a receptor composed of the low-affinity LIF receptor and gp130. This intermediate affinity receptor complex is capable of signalling and exerting biological effects in vitro. Although this receptor complex is shared by the two cytokines, the affinity of interaction and biological signals delivered by each of the cytokines are distinct. The third receptor recognized by OSM is a high affinity receptor that is not known to bind to other cytokines. The high affinity OSM receptor is composed of gp130 and an affinity-converting subunit that is required for high affinity and functional ligand-receptor binding.

4) IL-6

Interleukin-6 (IL-6) is a multifunctional cytokine that is produced by a variety of cells such as B-cells, T-cells, monocytes, fibroblasts and endothelial cells. IL-6 exhibits several activities relating to the proliferation and/or differentiation of hematopoietic progenitor cells. These activities result from IL-6 acting alone or in combination with other cytokines such as IL-3 and IL-4. Some specific biological effects of IL-6 include terminal differentiation of B-cells, proliferation and differentiation of T-cells, regulation of the acute phase response, growth regulation of epithelial cells, the differentiation of megakaryocytes, and thrombopoiesis. In accordance with these activities and effects, the target cells for IL-6 include B-cells, T-cells, myeloma cells, megakaryocytes, monocytes, early stem cells and hepatocytes.

Though IL-6 is a multifunctional cytokine, the various biological effects it exerts are believed to be initiated by the stepwise interaction of IL-6 with two distinct receptor subunits on a cell. IL-6 first forms a complex with an 80 kD receptor subunit. This complex binds to a non-ligand subunit, which is a membrane glycoprotein designated gp130. The binding of the IL-6-80 kD receptor complex to gp130 results in signal transduction.

5) sIL-6Rα

The receptor system for IL-6 comprises two functionally different chains: a ligand-binding chain (IL-6R) and a non-ligand-binding but signal-transducing chain (gp130). The gp130 chain associates with the IL-6R/IL-6 complex, resulting in the formation of high-affinity IL-6 binding sites and signal transduction. An extracellular, soluble form of the interleukin-6 receptor (sIL-6R) has been shown to mediate the IL-6 signal through membrane-anchored gp130.

6) IL-6/sIL-6Rα Chimera

A complex of sIL-6R and IL-6 (IL-6/sIL-6Rα chimera) can associate with gp130 expressed on both IL-6R-negative and IL-6R-positive cells. This association induces the homodimerization of gp 130 and the activation of the JAK-STAT pathway thereby leading to cellular response.

SUMMARY OF THE INVENTION

The present invention relates to a method of maturing an oocyte in vitro, comprising incubating an immature oocyte in a physiologically acceptable medium comprising an IL-6-type cytokine. The oocyte may be at the stage of an early antral or antral follicle. The IL-6-type cytokine may bind to a receptor including, but not limited to, LIFR-gp130 heterodimers, OSMR-gp130 heterodimers, and gp130 homodimers. The IL-6-type cytokine may not bind to a receptor including, but not limited to, IL-11Rα and CNTFRα. The IL-6-type cytokine may be LIF, CT-1, OSM, IL-6 or IL-6/sIL-6Rα. The medium used in the practice of the invention may further comprises FSH, hCG, or a combination thereof. Alternatively, the medium may not contain FSH, hCG, or a combination thereof.

The present invention also relates to a mature oocyte produced by a method comprising incubating an immature oocyte in a physiologically acceptable medium comprising an IL-6-type cytokine.

The present invention also relates to a method of in vitro fertilization comprising incubating sperm with a mature oocyte, wherein said mature oocyte is produced by a method comprising incubating an immature oocyte in a physiologically acceptable medium comprising an IL-6-type cytokine.

The present invention also relates to an embryo produced by a method comprising incubating sperm with a mature oocyte in vitro, wherein said mature oocyte is produced by a method comprising incubating an immature oocyte in a physiologically acceptable medium comprising an IL-6-type cytokine.

The present invention also relates to a method of treating infertility comprising implanting an embryo produced by a method comprising incubating sperm with a mature oocyte in vitro, wherein said mature oocyte is produced by a method comprising incubating an immature oocyte in a physiologically acceptable medium comprising an IL-6-type cytokine.

BRIEF DESCRIPTION OF THE DRAWINGS

FIG. 17 demonstrates the effect of LIF on birth rates.

DETAILED DESCRIPTION OF THE INVENTION

Figure 1:
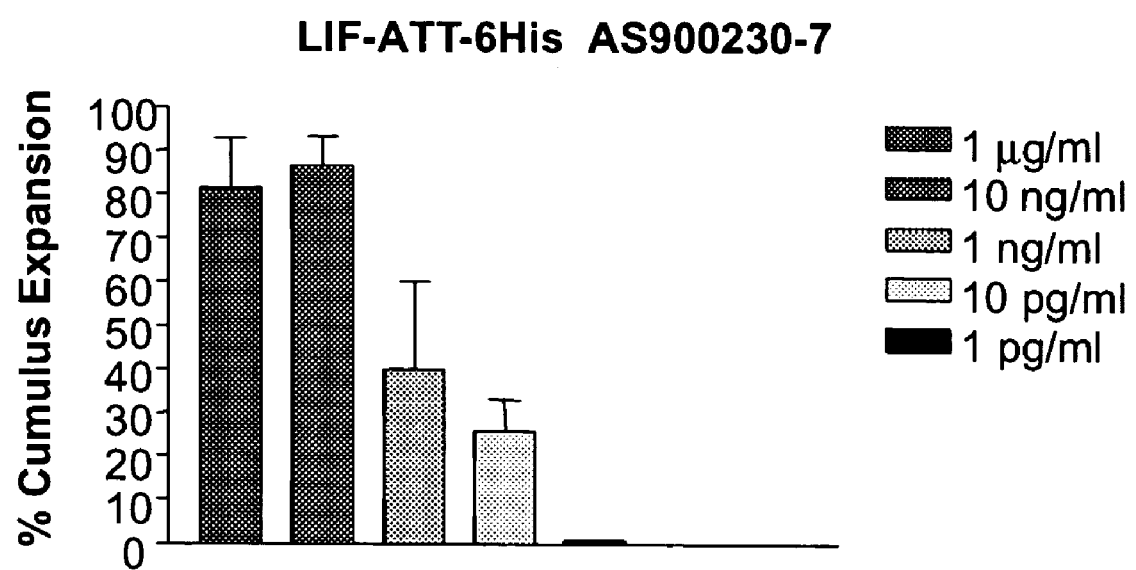
FIG. 1 depicts the dose response effect of AS900230-7 LIF on cumulus expansion.

As described above, the process of oogenesis is an extremely complex process related to the construction of an oocyte containing a large and complex dowry of resources for construction of the embryo.

1. In Vitro Maturation

The present invention is related to the use of certain IL-6-type cytokines for the in vitro maturation of oocytes.

a. Oocytes

The immature oocytes used in the practice of the present invention are retrieved from a female while the oocytes are at stages of development including, but not limited to, early antral and antral follicles.

The immature oocytes may be retrieved from a female that has not undergone external hormonal therapy. Alternatively, the immature oocytes may be retrieved from a female that has undergone external hormonal therapy. The female may have been administered hormones including, but not limited to, GnRH, FSH, LH or hCG. The hormones may have been administered in combination or sequentially in any order.

The immature oocytes may be retrieved from the female by methods including, but not limited to, echography and aspiration. The immature oocytes may be cryopreserved after isolation and thawed at a later time for in vitro maturation.

b. Maturation

The isolated immature oocytes are incubated in a culture medium comprising certain IL-6-type cytokines. The culture medium may be any physiologically acceptable culture medium including, but not limited to, TCM 199, aMEM and Ham's F10. The culture medium may further comprise other factors including, but not limited to, FSH, hCG, estradiol, cysteamine, sodium pyruvate, glutamine, and autologour heat-inactivated serum or follicular fluid. The culture medium may comprise certain IL-6-type cytokines together with FSH, hCG, estradiol, cysteamine, sodium pyruvate, glutamine, and autologour heat-inactivated serum or follicular fluid or a combination thereof. The culture medium may also comprise certain IL-6-type cytokines and be lacking FSH and/or hCG.

The immature oocytes are incubated in the culture medium at temperatures including, but not limited to, from about 37° C. to about 39° C. for a period of time including, but not limited to, about 6, 12, 18, 24, 30, 36, 42, 48, 54, 60, 66 or 72 hours. The oocytes are incubated until maturation has occurred as evidenced by methods including, but not limited to, visual inspection under microscope of germinal vesicle break down (GVBD), cumulus expansion, metaphase II plate formation (MII), polar body extrusion or functional tested by In Vitro Fertilization and Embryo Production.

c. Embryo Production

The mature oocytes may be incubated with sperm in vitro to produce mammalian embryos using standard in vitro fertilization methods (see Textbook of Assisted Reproductive Techniques Laboratory & Clinical Perspectives, edited by Gardner, et al., 2001 Martin Ldunetz Ltd., London). The embryo may be implanted into the uterus of a female capable of carrying the embryo to term.

2. IL-6 Cytokines

The IL-6-type cytokines used in the practice of present invention include, but are not limited to, those cytokines which bind to LIFR-gp130 heterodimers, OSMR-gp130 heterodimers, and gp130 homodimers. The IL-6-type cytokines used in the practice of present invention also include, but are not limited to, those cytokines which do not bind to IL-11Rα, and CNTFRα.

IL-6-type cytokines are a subfamily of the helix bundle cytokines that comprise four long a-helices termed A, B, C and D, which are arranged in a way that leads to an up-up-down-down topology. In contract with IL-6 and presumably also IL-11, where all the helices are straight, the A helix of LIF, OSM and CNTF is kinked. The straight cytokines may signal via gp130 homodimer, whereas the kinked cytokines may signal via LIFR-gp130 or OSMR-gp130 heterodimers. The IL-6-type cytokines used in the practice of present invention include, but are not limited to, IL-6, LIF, OSM, CT-1 and IL-6/sIL-6Rα chimera, as well as fragments, analogs, homologs, variants and derivatives thereof that retains a biological activity of said IL-6-type cytokine.

As used herein, the term "analog", when used in the context of an IL-6-type cytokine, means a peptide or polypeptide comprising one or more non-standard amino acids or other structural variations from the conventional set of amino acids.

As used herein, the term "derivative", when used in the context of an IL-6-type cytokine, means a peptide or polypeptide different other than in primary structure (amino acids and amino acid analogs). By way of illustration, derivatives may differ by being glycosylated, one form of post-translational modification. For example, peptides or polypeptides may exhibit glycosylation patterns due to expression in heterologous systems. If at least one biological activity is retained, then these peptides or polypeptides are derivatives according to the invention. Other derivatives include, but are not limited to, fusion peptides or fusion polypeptides having a covalently modified N- or C-terminus, PEGylated peptides or polypeptides, peptides or polypeptides associated with lipid moieties, alkylated peptides or polypeptides, peptides or polypeptides linked via an amino acid side-chain functional group to other peptides, polypeptides or chemicals, and additional modifications as would be understood in the art.

As used herein, the term "fragment", when used in the context of an IL-6-type cytokine, means a peptides of from about 8 to about 50 amino acids in length. The fragment may be 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids in length.

As used herein, the term "homolog", when used in the context of an IL-6-type cytokine, means a peptide or polypeptide sharing a common evolutionary ancestor.

As used herein, the term "variant", when used in the context of an IL-6-type cytokine, means a peptide or polypeptide that differs in amino acid sequence by the insertion, deletion, or conservative substitution of amino acids, but retain at least one biological activity. For purposes of the present invention, "biological activity" includes, but is not limited to, the ability to be bound by a specific antibody.

A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., *J. Mol. Biol.* 157: 105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ∀ 2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated herein by reference. Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

Additionally, computerized algorithms are available to assist in predicting amino acid sequence domains likely to be accessible to an aqueous solvent. These domains are known in the art to frequently be disposed towards the exterior of a peptide, thereby potentially contributing to binding determinants, including antigenic determinants.

The present invention has multiple aspects, illustrated by the following non-limiting examples.

Example 1

Effect of LIF on the In Vitro Cumulus Expansion of the Cumulus-Oocyte Complex

The ability of LIF to induce cumulus expansion of murine COCs in vitro was assayed. Seven to eight-week-old CD-1 female mice (Charles River) were primed with PMSG (5 IU/female, Calbiochem). The females were sacrificed 48 hours later by progressive hypoxemia. Alcohol (70%) was applied to the animals' abdominal region to clean the area and also to decrease contamination of samples with hair. A ventral incision was made to expose the abdominal cavity. The ovaries connected to oviducts were cut away from the uterine horn and the visceral adipose tissue. Ten ovaries were added to tubes (Corning) containing 3 ml of L-15 medium (Gibco) plus 10% fetal calf serum (FCS) and maintained at 37° C.

The contents of each tube was later transferred to a 60×15 mm Petri dish (Falcon). The ovaries were cleaned of the fatty pad and oviduct by means of scissors or 27 gauge needles under a stereomicroscope (Nikon SM-2-800) with thermoplate heating stage. The cleaned ovaries were then placed in a new Petri dish filled with 2-3 ml of fresh medium (L15+10% FCS).

COCs were recovered by mechanical rupture of each ovary with needles and placed in a new 35×10 mm Petri dish filled with fresh medium (L15+10% FCS). Cumulus-intact oocytes were selected on the basis of homogenous cytoplasm using a low-power (20-30×) stereomicroscope. Two COCs were transferred by mouth glass pipet to each well of a 96-well plate containing 90 µl culture media (αMEM [Gibco] with 10% FCS and PenStrep-Antibiotics [Invitrogen]) without mineral oil. Before addition of the COCs to the 96-well plate, the medium in the plate was pre-equilibrated for a period of 1 hour at 37° C. in a humidified incubator with 5% $CO_2$. After addition of the COCs to each well, different lots of LIF were added in a volume of 10 µl so that the final volume in each well was 100 µl. Each 96-well plate contained 4 wells of a "Negative Control" containing AMEM and FCS, and 4 wells of a "Positive Control" containing αMEM, FCS and 5 ng/ml EGF (Sigma). Two plates, duplicates, were run per assay. The plate were incubated for 18 hours at 37° C. in a humidified incubator with 5% $CO_2$.

Each COC was then visually inspected using a Nikon Inverted Microscope to identify the formation of a mucoid extracellular matrix by cumulus cells, which is an indicator of cumulus expansion. The percentage of cumulus expansion was defined as the number of expanded COCs in relation to the total COCs that were used in each treatment group. If any lot of LIF induced greater than 50% COC expansion, it was considered to be positive and then all forms of LIF were retested in a reconfirmation assay. Confirmed positives lots of LIF were then evaluated in dose-response tests. Dose-response testing was performed as described, but 3 wells with 4 to 5 COCs per well were assigned to each concentration of LIF.

The rates of in vitro maturation for different forms and lots of LIF are shown in Table 1. Most of the LIF forms and lots tested induced cumulus expansion (20 to 100% expansion). Only AS900227-1 at the concentration tested failed to induce cumlus expansion.

TABLE 1

| IVM Primary Screen | | | | | |
|---|---|---|---|---|---|
| LIF# - lot # | Form | Origin | Total Oocytes | Expanded Oocytes | % Expansion[1] |
| AS900230-1 | LIF-ATT-6HIS | HEK cells | 5 | 5 | 100% |
| AS900230-2 | LIF-ATT-6HIS | HEK cells | 5 | 5 | 100% |

TABLE 1-continued

IVM Primary Screen

| LIF# - lot # | Form | Origin | Total Oocytes | Expanded Oocytes | % Expansion[1] |
|---|---|---|---|---|---|
| AS900230-3 | LIF-ATT-6HIS | HEK cells | 5 | 5 | 100% |
| AS900230-4 | LIF-ATT-6HIS | HEK cells | 5 | 4 | 80% |
| AS900230-5 | LIF-ATT-6HIS | HEK cells | 4 | 4 | 100% |
| AS900230-6 | LIF-ATT-6HIS | HEK cells | 4 | 2 | 50% |
| AS900230-7 | LIF-ATT-6HIS | HEK cells | 5 | 5 | 100% |
| AS900230-8 | LIF-ATT-6HIS | HEK cells | 4 | 2 | 20% |
| AS900227-1 | LIF-6HIS | HEK cells | 4 | 0 | 0% |
| AS900227-4 | LIF-6HIS | HEK cells | 4 | 2 | 50% |
| AS900001-2 | LIF (clinical grade) | E. coli | 4 | 1 | 25% |

[1]positive controls were 100% and negative controls were 0%

As a reconfirmation of positives in the IVM Primary Screen, 2 LIF formulations (AS900230-1 and AS900227-4) were evaluated against two commercial forms of LIF (Antigenix and Calbiochem). The results of the reconfirmation IVM assays are shown in Table 2.

TABLE 2

Reconfirmation IVM Assay

| LIF# - lot # | Origin | Total Oocytes | Expanded Oocytes | % Expansion[1] |
|---|---|---|---|---|
| AS900230-1 | Serono | 5 | 5 | 100% |
| AS900227-4 | Serono | 5 | 4 | 80% |
| LIF | Calbiochem | 5 | 3 | 60% |
| LIF | Antigenix | 5 | 5 | 100% |

[1]positive controls were 100% and negative controls were 0%

Figure 2:
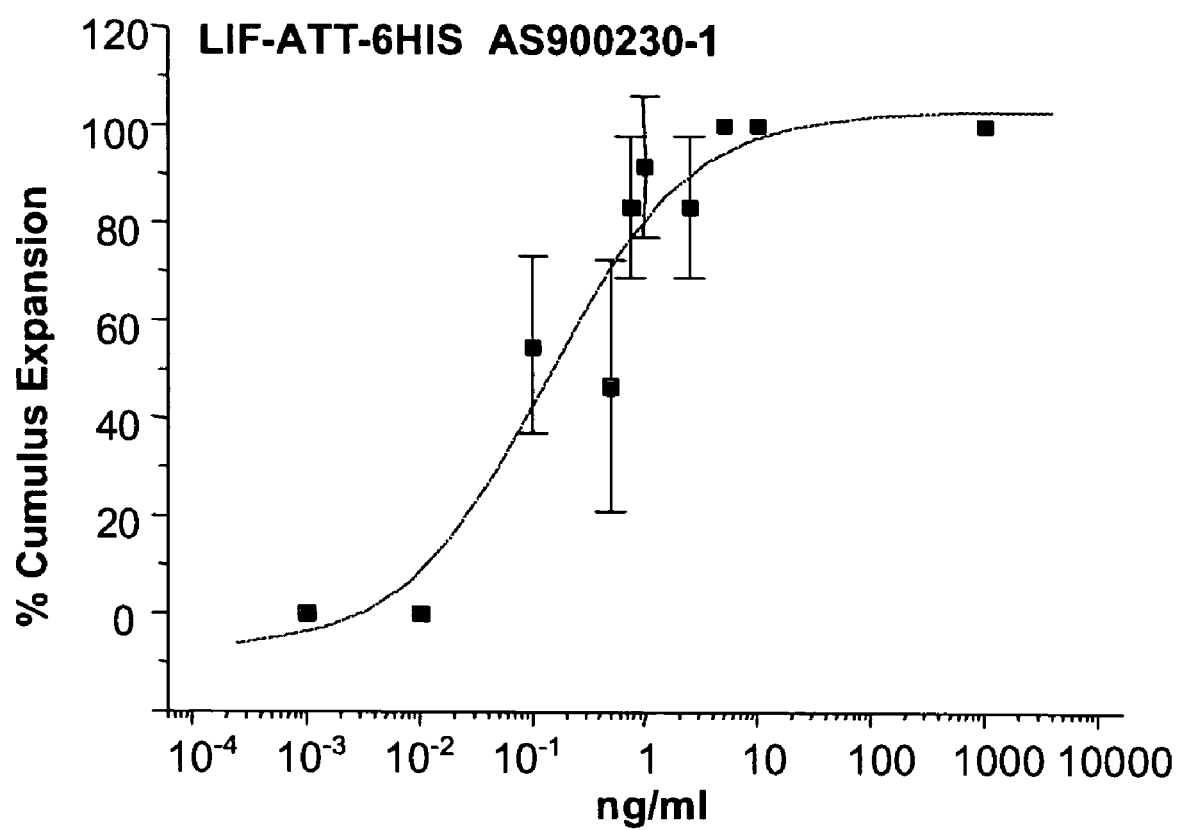
FIG. 2 depicts the dose response effect of AS900230-1 LIF on cumulus expansion.
Figure 3:
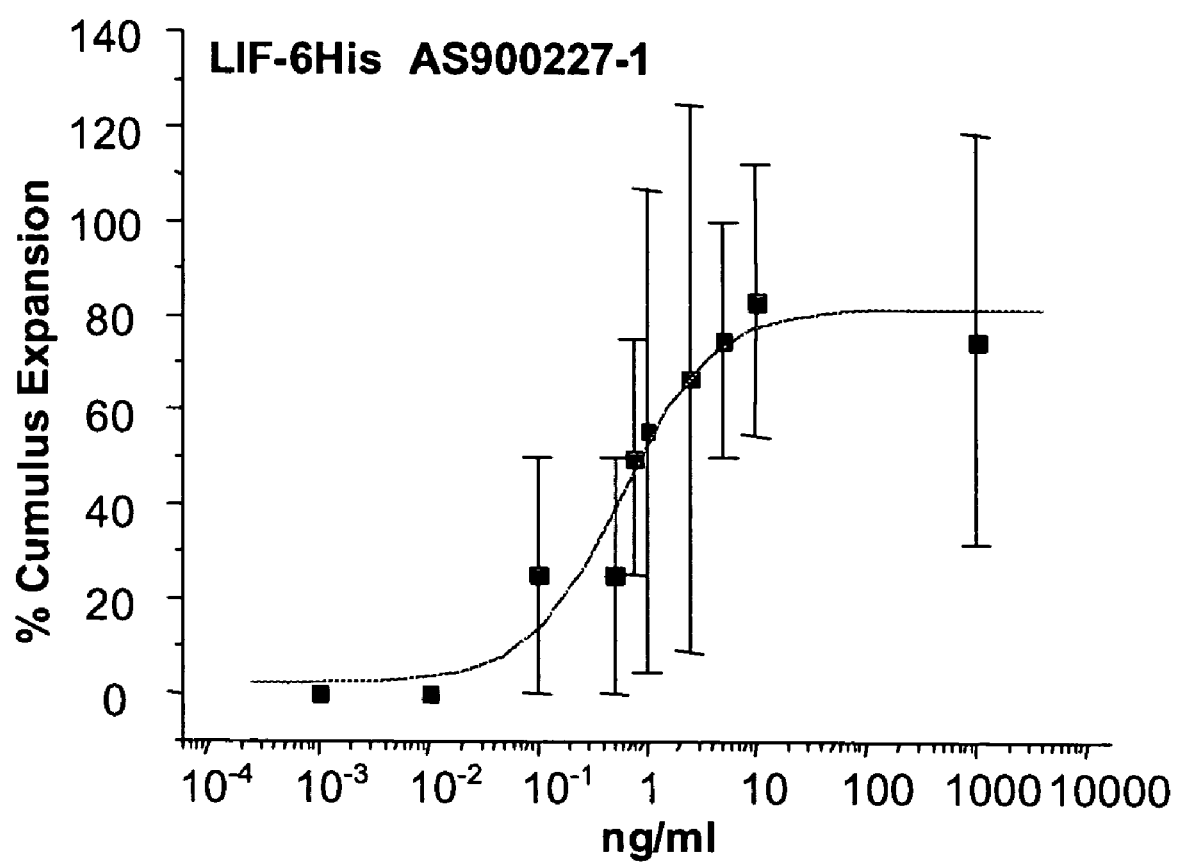
FIG. 3 depicts the dose response effect of A900227-1 LIF on cumulus expansion.
Figure 4:
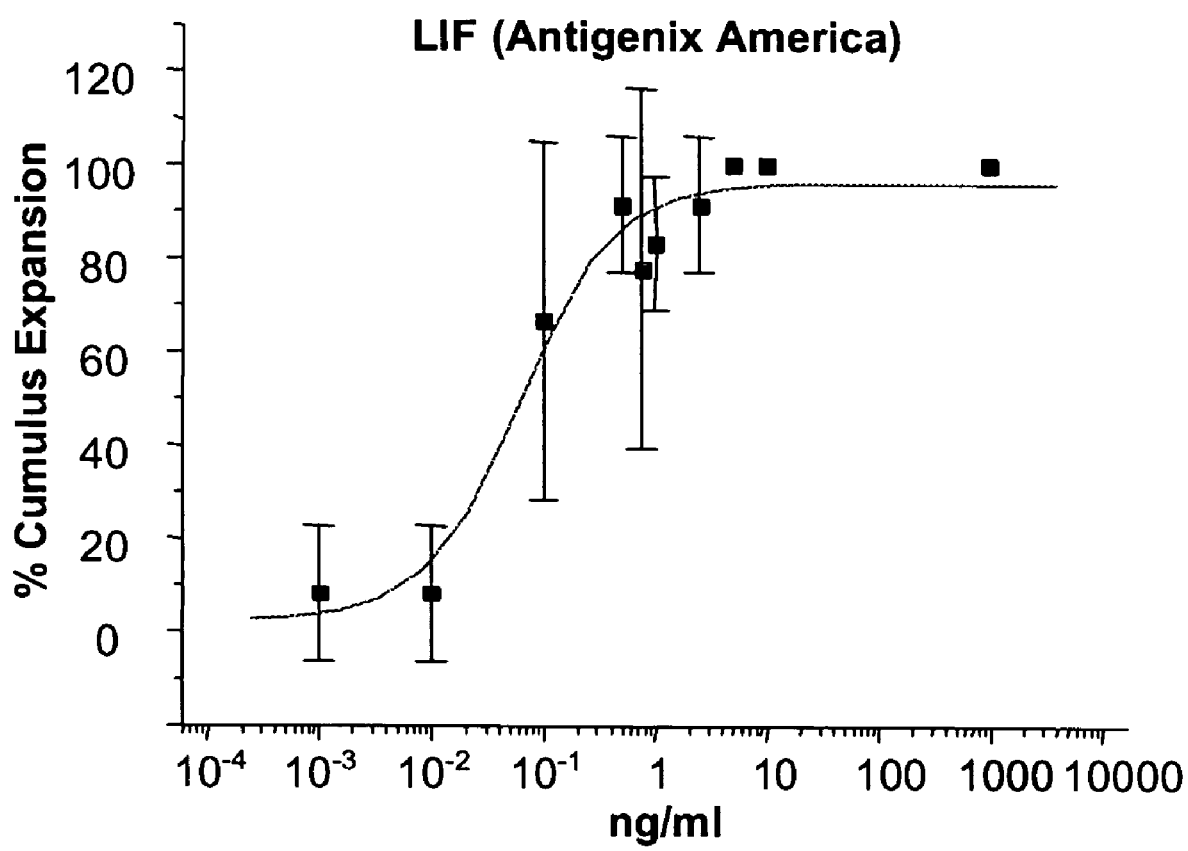
FIG. 4 depicts the dose response effect of LIF on cumulus expansion.

Based on the positive results in the IVM Primary Screen and the Reconfirmation IVM assays, dose-response analysis was performed for AS900230-7 (FIG. 1), AS900230-1 (FIG. 2), AS900227-1 (FIG. 3) and LIF from Antigenix (FIG. 4). Although AS900227-1 was the only LIF unable to induce cumulus expansion in the IVM primary screening, it was able to induce cumulus expansion in dose-response testing in a dose-responsive manner. The lack of 50% expansion in the primary screen by AS900227-1 may have been due to problems with dilution.

Example 2

Effect of CT-1 and OSM on the In Vitro Maturation of the Cumulus-Oocyte Complex

Figure 5:
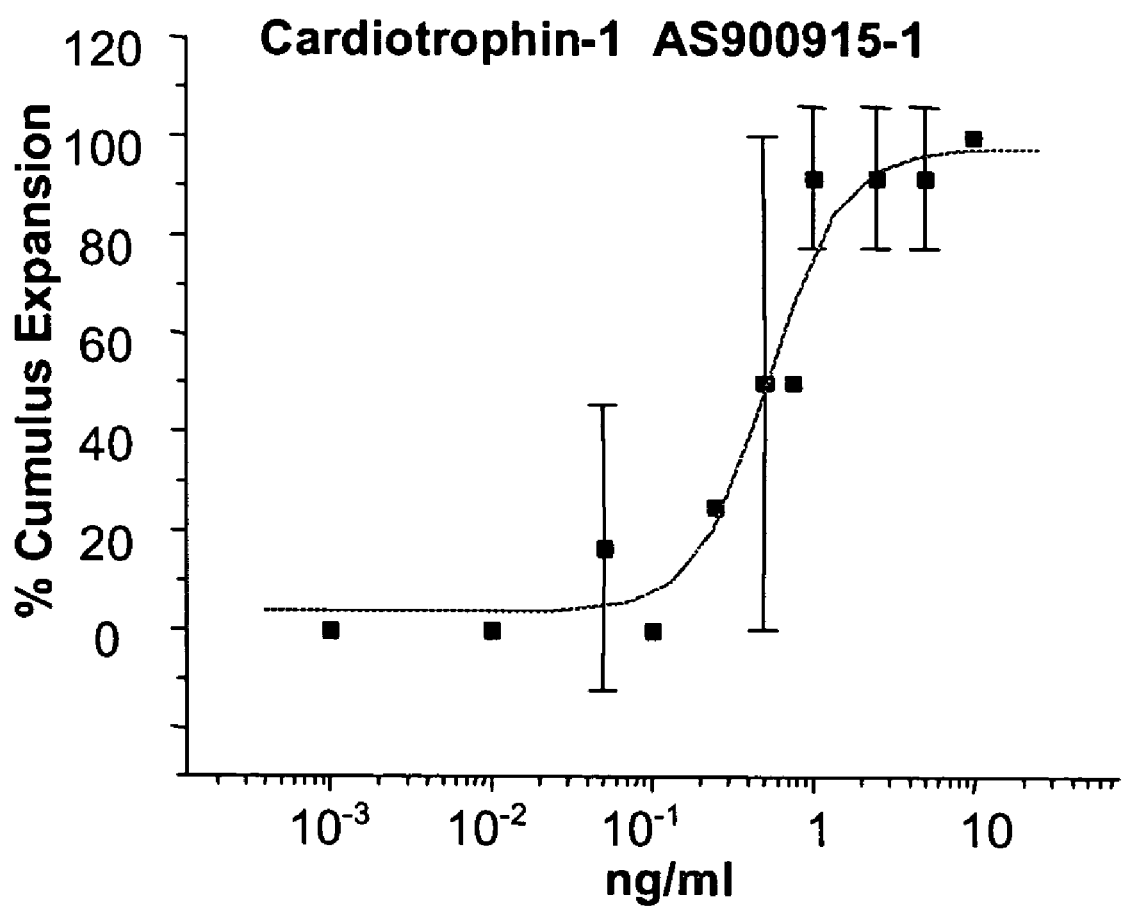
FIG. 5 depicts the dose response effect of AS900915-1 CT-1 on cumulus expansion.
Figure 6:
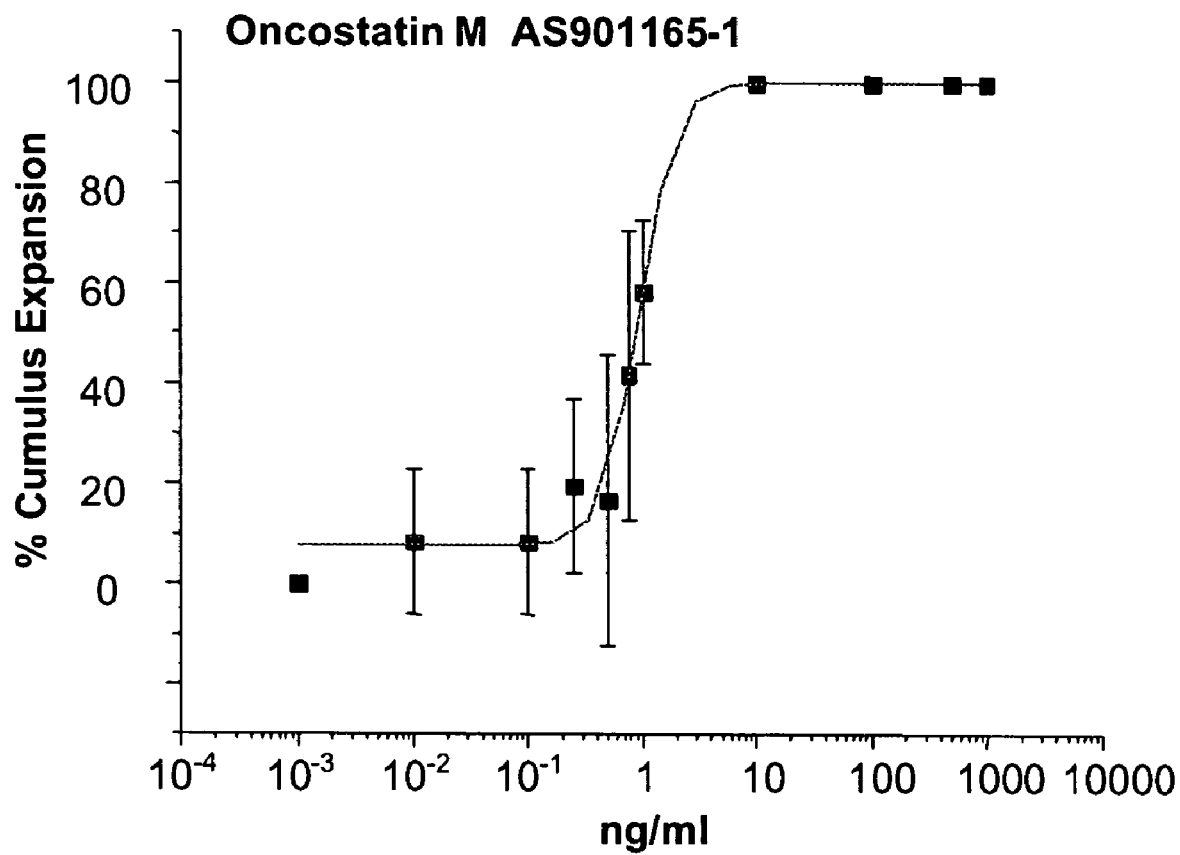
FIG. 6 depicts the dose response effect of AS901a65-1 oncostatin on cumulus expansion.

The ability of CT-1 and OSM to induce in vitro cumulus expansion of COCs was assayed in the manner described in Example 1. As shown in Table 3, murine CT-1 (Preprotech, Cat # 250-25, lot 021203) and human OSM AS901165-1 (Calbiochem Cat # 496260, lot B30866) induced 100% of cumulus expansion at 1 μg/ml and 500 ng/ml. Based on the positive results for murine CT-1 and human OSM, the IVM assay was repeated at varying concentrations to determine the dose response of human CT-1 (AS900915-1) (FIG. 5) and OSM (AS901165-1; FIG. 6).

TABLE 3

IVM Assay

| IL-6 Family | Concent. | Expand | Total | %[1] | Average | Stdv |
|---|---|---|---|---|---|---|
| Murine CT-1 (Cardiotrophin-1) | 1 μg/ml | 3 | 3 | 100 | | |
| | | 3 | 3 | 100 | 100.0 | 0.0 |
| | 500 ng/ml | 3 | 3 | 100 | | |
| | | 3 | 3 | 100 | 100.0 | 0.0 |
| OSM (Oncostatin M) | 1 μg/ml | 3 | 3 | 100 | | |
| | | 3 | 3 | 100 | 100.0 | 0.0 |
| | 500 ng/ml | 3 | 3 | 100 | | |
| | | 3 | 3 | 100 | 100.0 | 0.0 |

Total = Total Oocytes evaluated
Expand = Number of Expanded Oocytes
[1]positive controls were 100% and negative controls were 0%

Example 3

Comparison of Human CT-1 and Murine CT-1

Another IVM assay was performed to compare the dose response of murine CT-1 vs. human CT-1. The results in Table 4 indicate that both human CT-1 and murine CT-1 induce in vitro cumulus expansion of COCs.

TABLE 4

IVM Assay

| IL-6 Family | Concent. | Expand | Total | %[1] | Average | Stdv |
|---|---|---|---|---|---|---|
| Murine CT-1 (Cardiotrophin-1) | 1 μg/ml | 2 | 2 | 100 | | |
| | | 2 | 2 | 100 | 100.0 | 0.00 |
| | 100 ng/ml | 2 | 2 | 100 | | |
| | | 2 | 2 | 100 | 100.0 | 0.00 |
| | 10 ng/ml | 2 | 2 | 100 | | |
| | | 2 | 2 | 100 | 100.0 | 0.00 |
| | 1 ng/ml | 1 | 2 | 50 | | |
| | | 1 | 2 | 50 | 50.0 | 0.00 |
| Human CT-1 (Cardiotrophin-1) AS900915-1 | 1 μg/ml | 2 | 2 | 100 | | |
| | | 2 | 2 | 100 | 100.0 | 0.0 |
| | 100 ng/ml | 2 | 2 | 100 | | |
| | | 2 | 2 | 100 | 100.0 | 0.0 |
| | 10 ng/ml | 2 | 2 | 100 | | |
| | | 2 | 2 | 100 | 100.0 | 0.0 |
| | 1 ng/ml | 0 | 2 | 0 | | |
| | | 0 | 2 | 0 | 0.0 | 0.0 |

Total = Total Oocytes evaluated
Expand = Number of Expanded Oocytes
[1]positive controls were 100% and negative controls were 0%

Example 4

Effect of IL-6 and sIL-6Rα on the In Vitro Maturation of the Cumulus-Oocyte Complex Based on the ability of LIF, CT-1 and OSM to induce in vitro cumulus expansion of COCs as shown in Examples 1-3, we also tested IL-6 and sIL-6Rα. The results in Table 5 indicate that IL-6 and sIL-6Rα also induce in vitro cumulus expansion.

TABLE 5

IVM Assay

| IL-6 Family | Concent. | Expand | Total | %[1] | Average | Stdv |
|---|---|---|---|---|---|---|
| IL-6 (Peprotech) | 2 µg/ml | 4 | 4 | 100 | | |
| | | 2 | 3 | 67 | 83.3 | 23.6 |
| | 1 µg/ml | 1 | 3 | 33 | | |
| | | 2 | 3 | 67 | 50.0 | 23.6 |
| | 500 ng/ml | 0 | 3 | 0 | | |
| | | 0 | 3 | 0 | 0.0 | 0.0 |
| sIL-6Rα (Peprotech) | 2 µg/ml | 2 | 3 | 67 | | |
| | | 1 | 3 | 33 | 50.0 | 23.6 |
| | 1 µg/ml | 0 | 3 | 0 | | |
| | | 0 | 3 | 0 | 0.0 | 0.0 |
| | 500 ng/ml | 1 | 3 | 33 | | |
| | | 1 | 3 | 33 | 33.3 | 0.0 |

Total = Total Oocytes evaluated
Expand = Number of Expanded Oocytes
[1]positive controls were 100% and negative controls were 0%

Figure 7:
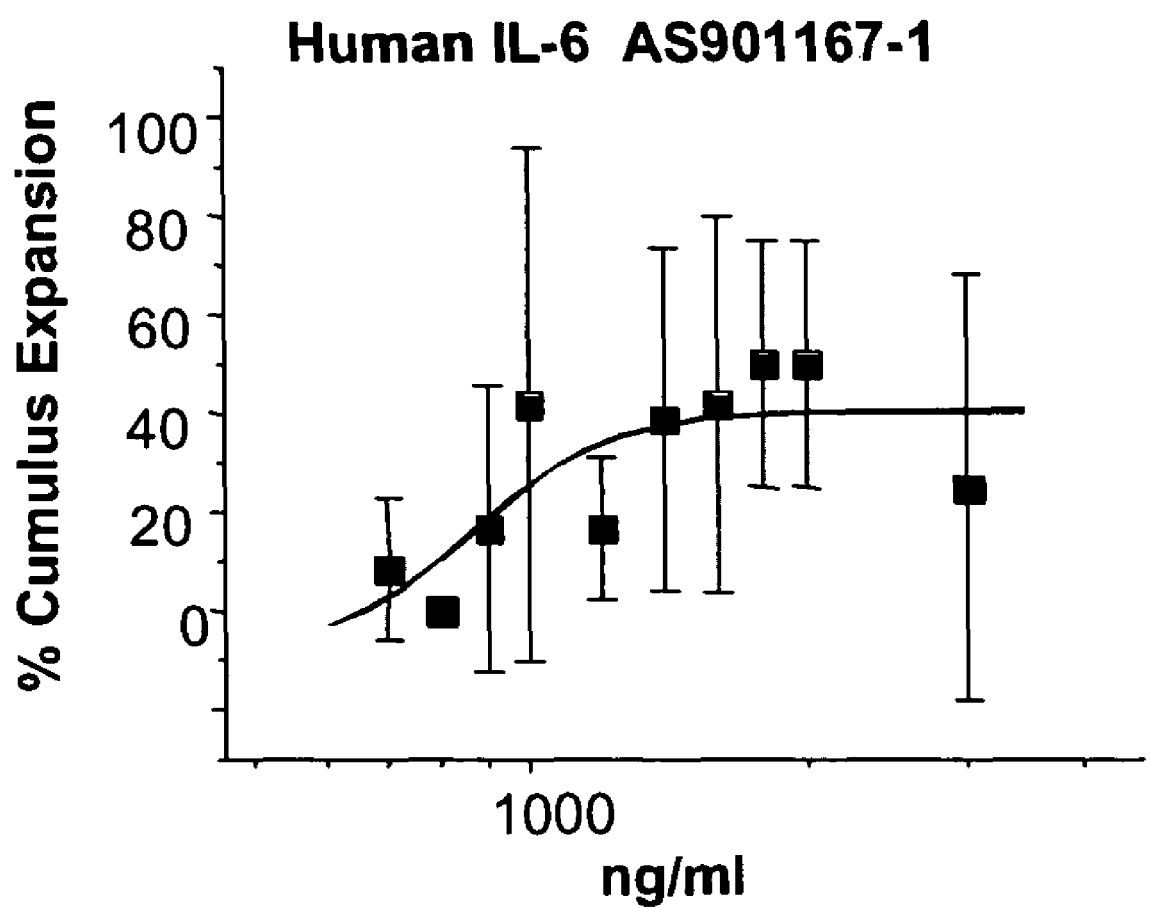
FIG. 7 depicts the dose response effect of AS901167-1 human IL-6 on cumulus expansion.
Figure 8:
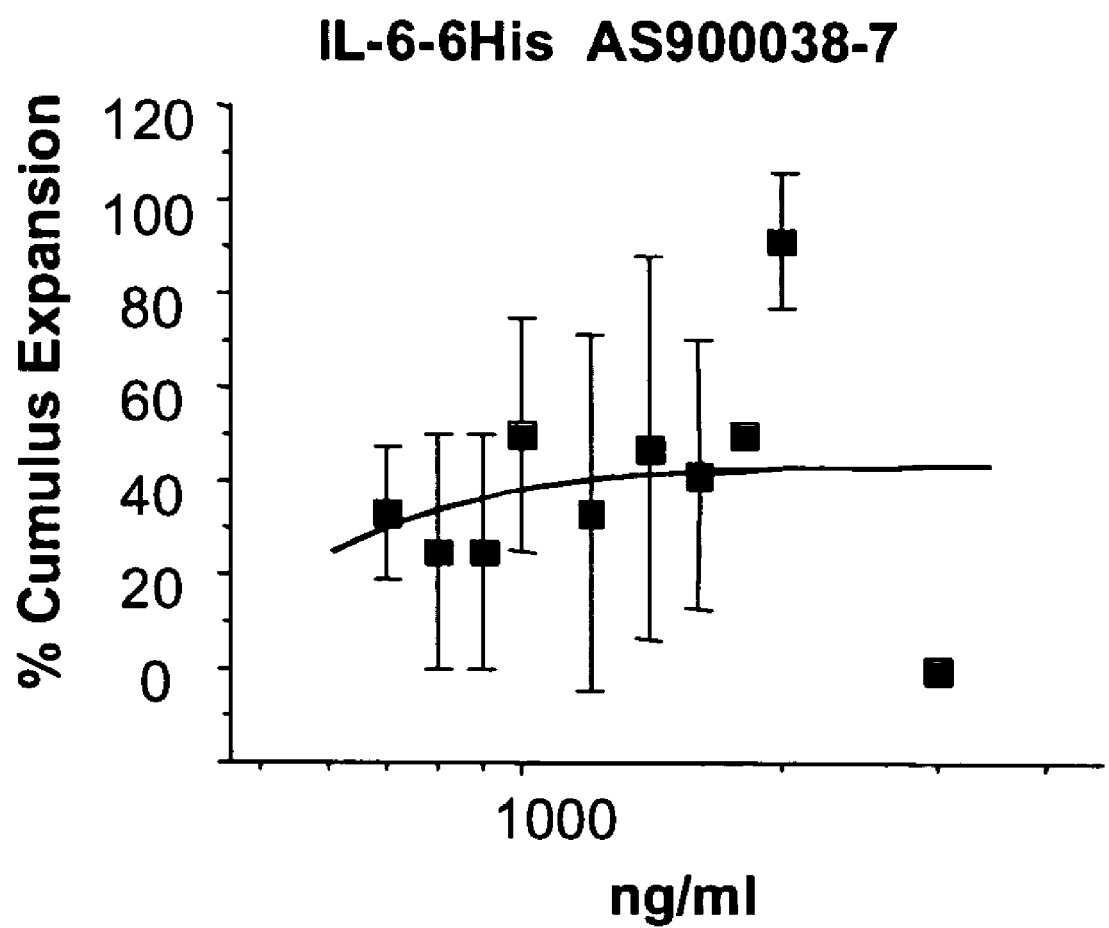
FIG. 8 depicts the dose response effect of AS900038-7 human IL-6 on cumulus expansion.
Figure 9:
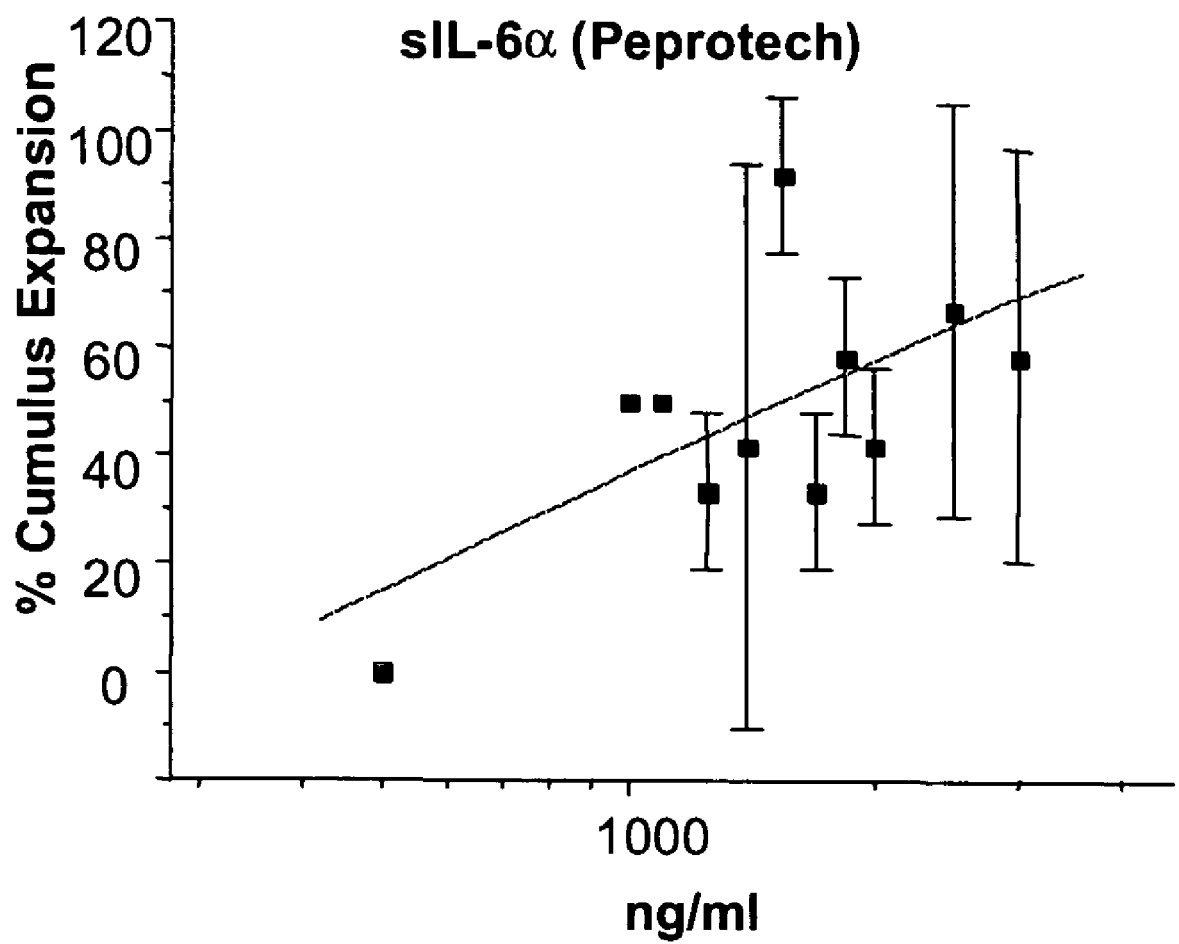
FIG. 9 depicts the dose response effect of sIL-6Rα on cumulus expansion.
Figure 10:
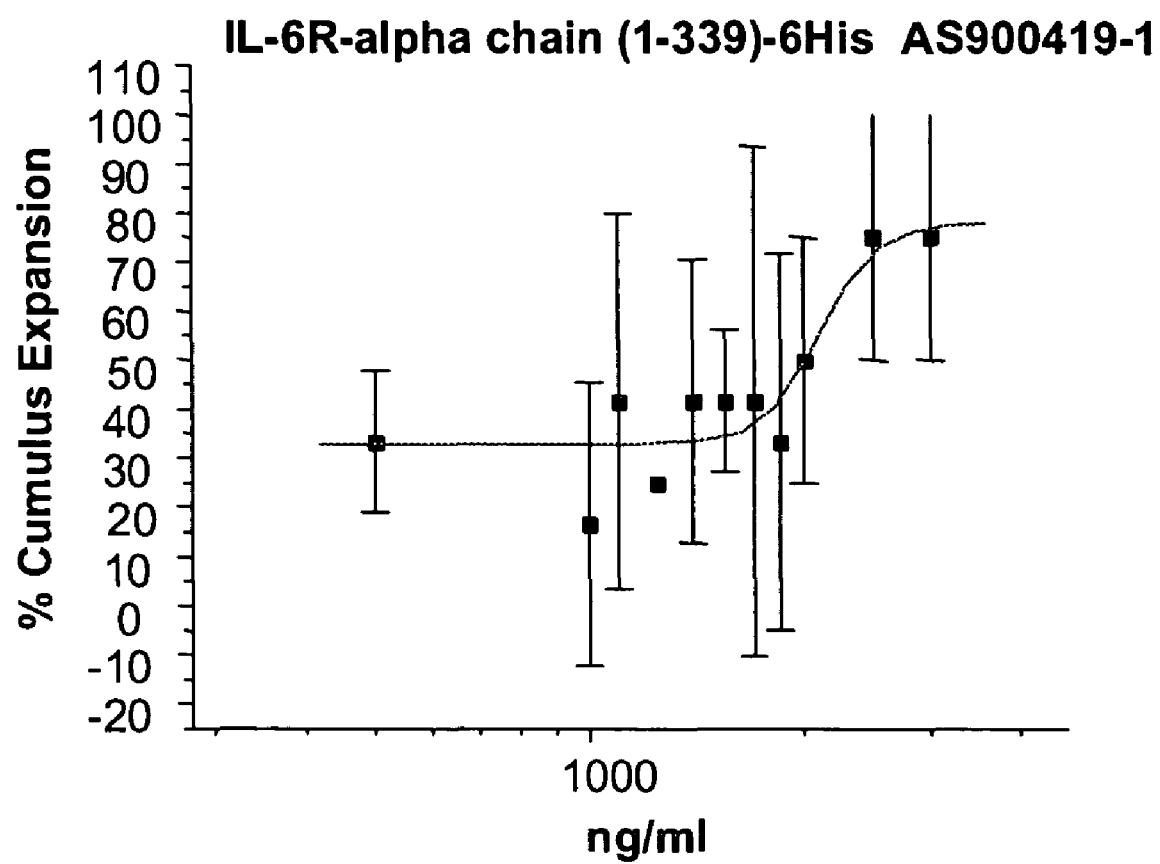
FIG. 10 depicts the dose response effect of AS900419 IL-6Rα (1-339)-6His on cumulus expansion.

Based on the above results, an additional IVM assay was performed to determine the dose response of different forms of IL-6 (Table 6). FIGS. 7-8 show that moderate cumlus expansion occurs with relatively higher amounts of IL-6. FIGS. 9-10 show the dose response for different forms of sIL-6Rα.

TABLE 6

IVM Assay

| IL-6 Family | Concent. | Expand | Total | %[1] | Average | Stdv |
|---|---|---|---|---|---|---|
| IL-6 (Peprotech) | 3 µg/ml | 4 | 4 | 100 | | |
| | | 4 | 4 | 100 | | |
| | | 4 | 4 | 100 | 100.0 | 0.0 |
| | 1.8 µg/ml | 4 | 4 | 100 | | |
| | | 3 | 4 | 75 | | |
| | | 2 | 4 | 50 | 75.0 | 25.0 |
| | 1.4 µg/ml | 1 | 4 | 25 | | |
| | | 4 | 4 | 100 | | |
| | | 2 | 4 | 50 | 58.3 | 38.2 |
| | 1 µg/ml | 1 | 4 | 25 | | |
| | | 2 | 4 | 50 | | |
| | | 2 | 4 | 50 | 41.7 | 14.4 |
| IL-6 (AS900073-2) | 3 µg/ml | 0 | 4 | 0 | | |
| | | 0 | 4 | 0 | 0.0 | 0.0 |
| | 2 µg/ml | 2 | 4 | 50 | | |
| | | 0 | 4 | 0 | 25.0 | 35.4 |
| | 1 µg/ml | 0 | 4 | 0 | | |
| | | 1 | 4 | 25 | 12.5 | 17.6 |
| IL-6-D-ATT-6His (AS900226-1) | 3 µg/ml | 0 | 4 | 0 | | |
| | | 0 | 4 | 0 | 0.0 | 0.0 |
| | 2 µg/ml | 4 | 4 | 100 | | |
| | | 0 | 4 | 0 | 50.0 | 70.7 |
| | 1 µg/ml | 1 | 4 | 25 | | |
| | | 0 | 4 | 0 | 12.5 | 17.6 |

Total = Total Oocytes evaluated
Expand = Number of Expanded Oocytes
[1]positive controls were 100% and negative controls were 0%

Example 5

Figure 11:
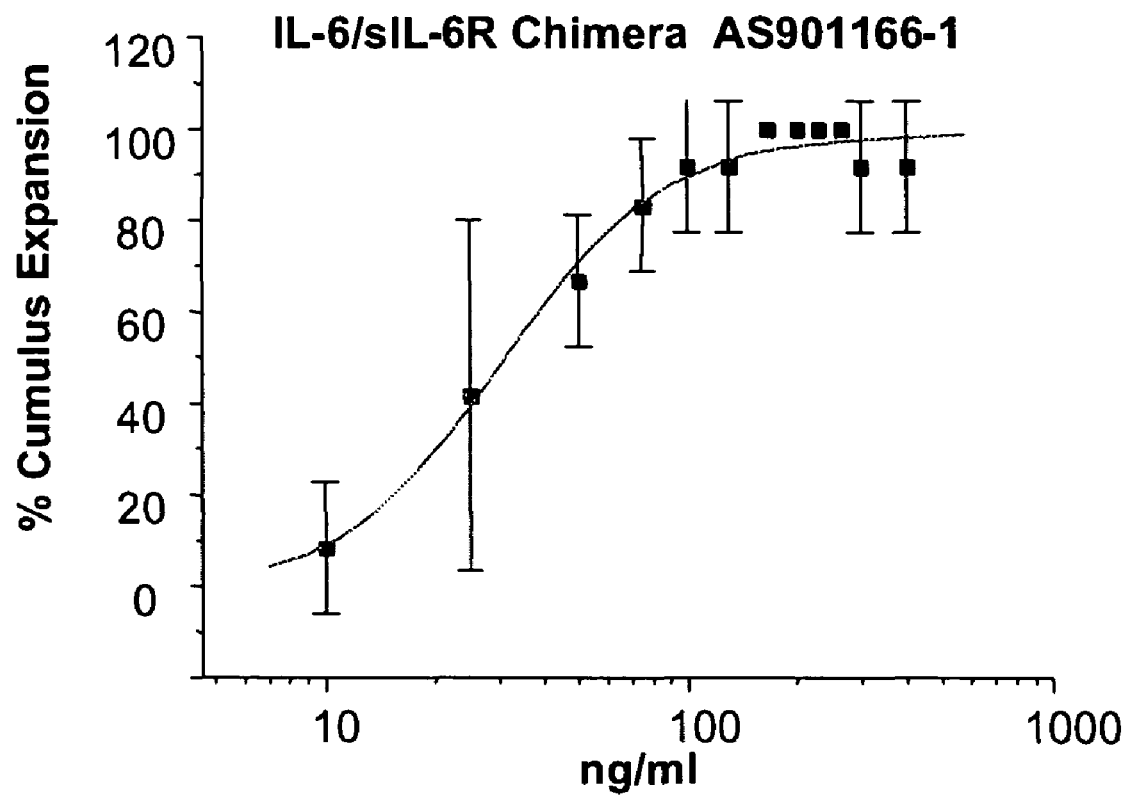
FIG. 11 depicts the dose response effect of AS901166 IL-6/sIL-6Rα chimera on cumulus expansion.

Effect of IL-6/sIL-6Rα on the In Vitro Maturation of the Cumulus-Oocyte Complex Based on the ability of IL-6 and sIL-6Rα to individually induce in vitro cumulus expansion of COCs as shown in Example 4, we tested the ability of the IL-6/sIL-6Rα chimera to induce in vitro cumlus expansion. Table 7 shows that the IL-6/sIL-6Rα chimera was able to induce in vitro cumlus expansion of COCs. The dose response of the IL-6/sIL-6Rα chimera in FIG. 11 indicates that the chimera is more potent than IL-6 or sIL-6Rα at inducing in vitro cumlus expansion. Moreover, the induction by IL-6/sIL-6Rα is less variable.

TABLE 7

IVM Assay

| IL-6 Family | Concent. | Expand | Total | %[1] | Average | Stdv |
|---|---|---|---|---|---|---|
| IL-6/sIL-6Rα | 3 µg/ml | 4 | 4 | 100 | | |
| | | 4 | 4 | 100 | 100.0 | 0.0 |
| | 2 µg/ml | 4 | 4 | 100 | | |
| | | 4 | 4 | 100 | 100.0 | 0.0 |
| | 1 µg/ml | 4 | 4 | 100 | | |
| | | 4 | 4 | 100 | 100.0 | 0.0 |

Total = Total Oocytes evaluated
Expand = Number of Expanded Oocytes
[1]positive controls were 100% and negative controls were 0%

Example 6

Effect of LIF on Quality of In Vitro-Matured Oocytes

As shown in Examples 1-5, IL-6-type cytokines induce in vitro maturation of oocytes. stimulate cumulus expansion in a dose-dependent manner. We next tested the effects of an IL-6-type cytokine on the quality of in vitro matured oocytes by measuring fertilization rate, blastocyst rate and birth rate.

Murine COCs were isolated from seven to eight-week-old B6CBAF1/J female mice (Jackson labs) as described in Example 1. The recovered COCs were matured in vitro, as described above, in IVM containing 1.5 IU/ml of rhCG (recombinant human chorionic gonadotropins). Replicates of experiments were performed on different days with different batches of oocytes. Oocytes were matured in the presence of 1000, 1 or 0.1 ng/ml of LIF (Antigenix America, HC88832), with or without 0.2 IU of rFSH (recombinant human follicle stimulating hormone). A negative control group (IVM medium without LIF and FSH) and a positive control group (in vivo-matured oocytes=ovulated oocytes) were included. In vitro-matured oocytes were prepared by administering PMSG to mice followed 48 hours later with 5 IU of hCG (ip). 18 hours after hCG priming (day of the in vitro fertilization), the females were sacrificed and the ovaries and oviducts removed. The expanded COCs were obtained by mechanical rupture.

In vitro- and in vivo-matured COCs were washed in in-vitro fertilization (IVF) medium (KSOM supplemented with 3% BSA Fraction V [Sigma]) then placed in 50 µl microdrops under mineral oil. Spermatozoa were then added at a concentration of $2 \times 10^6$/ml. Epididymal sperm suspensions were prepared from adult male mice and pre-incubated for 2 hours in IVF medium to ensure capacitation. The sperm and oocytes were incubated for 4-5 hours, after which COCs were removed, washed, denuded of cumulus cells and placed into 30 μl microdroplets of in vitro embryo culture (IVC) medium (KSOM supplemented with 0.5% Fraction V crystalline BSA [Calbiochem]) under mineral oil into a humidified 5% $O_2$, 5% $CO_2$ and 90% $N_2$ incubator at 37° C.

Figure 12:
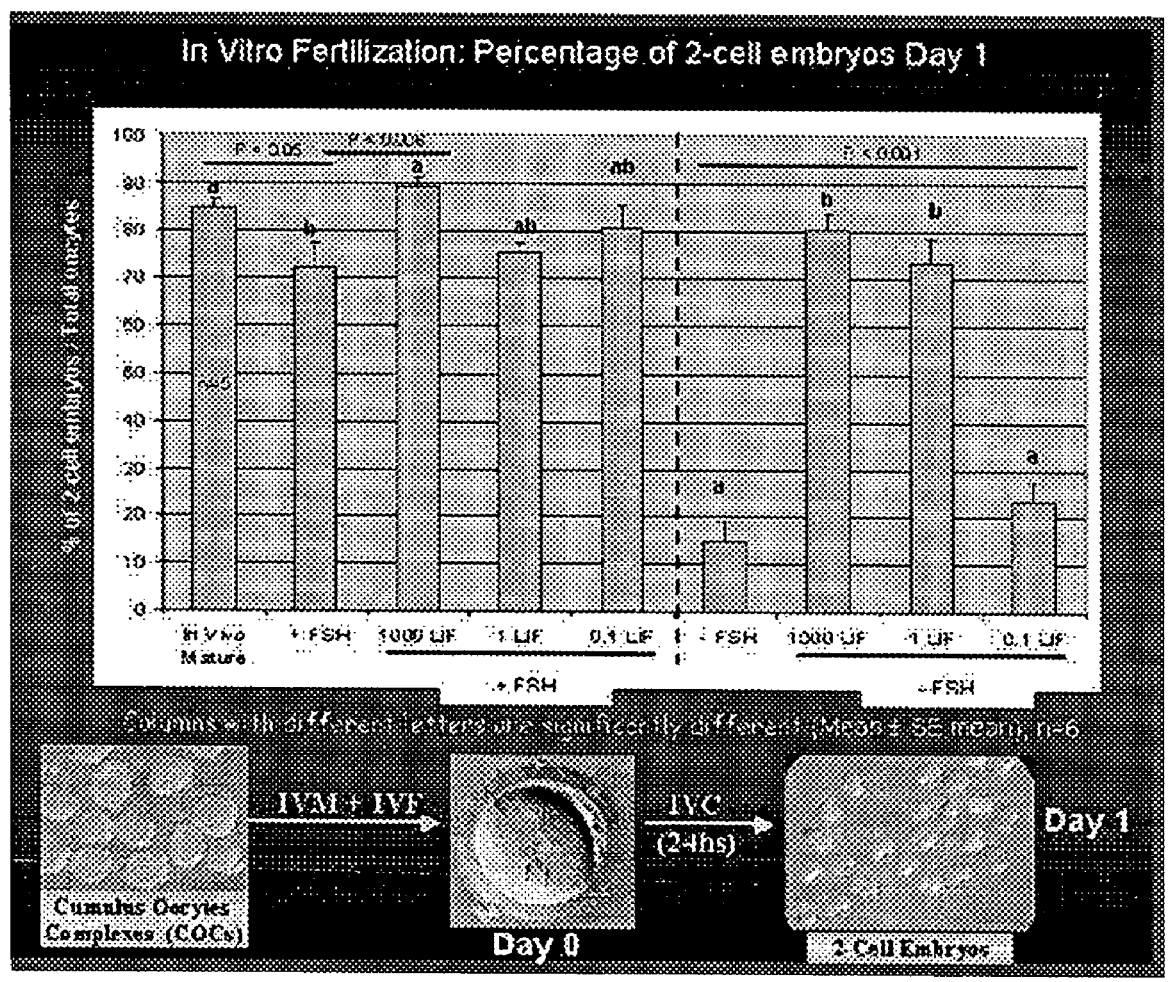
FIG. 12 demonstrates the effect of LIF on the rate of in vitro fertilized oocytes.
Figure 13:
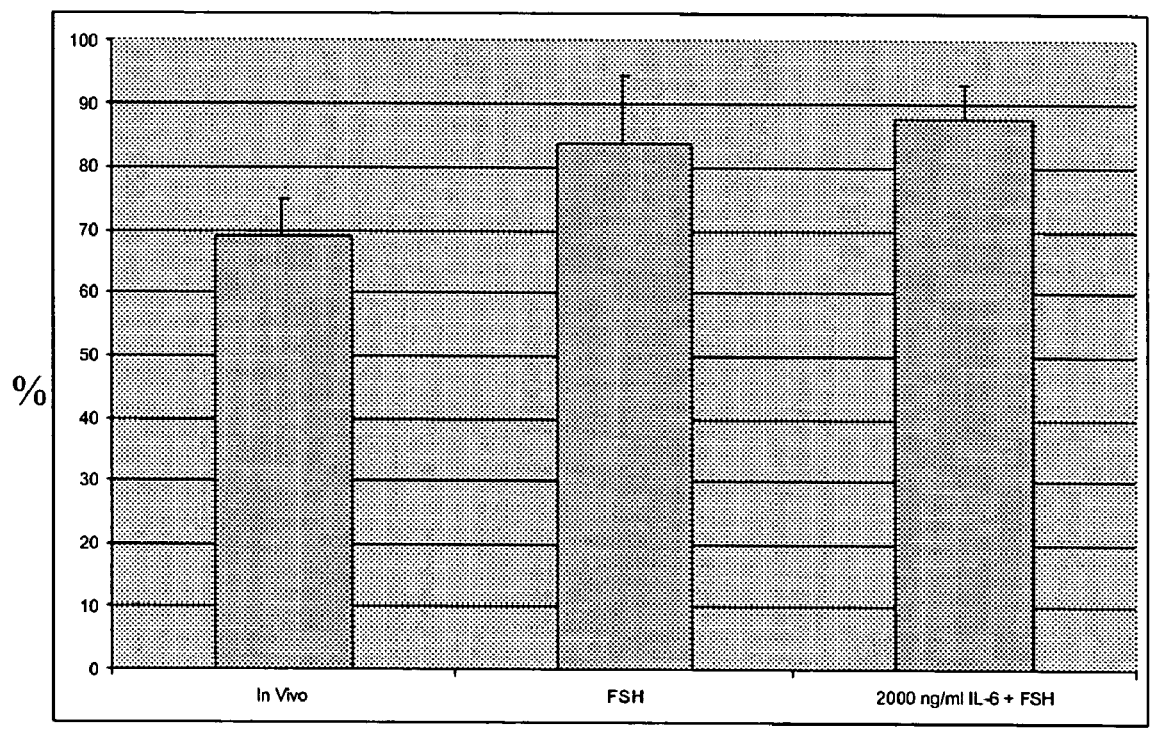
FIG. 13 demonstrates the effect of LIF on the rate of in vitro fertilized oocytes.

The rate of in vitro fertilization was measured at Day 1 based on the percentage of 2-cell embryos. As shown in FIG. 12, there was a significant increase in the fertilization rate in the (1000 ng/ml of LIF+FSH)-IVM group and in the in vivo-matured group when compared with the FSH-IVM group. A similar increase in the fertilization rate was seen with 2000 ng/ml of LIF+FSH (FIG. 13). LIF (1000 or 1 ng/ml) alone also produced a significant increase in the fertilization rate compared with the negative control (IVM medium without FSH) (FIG. 12).

Figure 14:
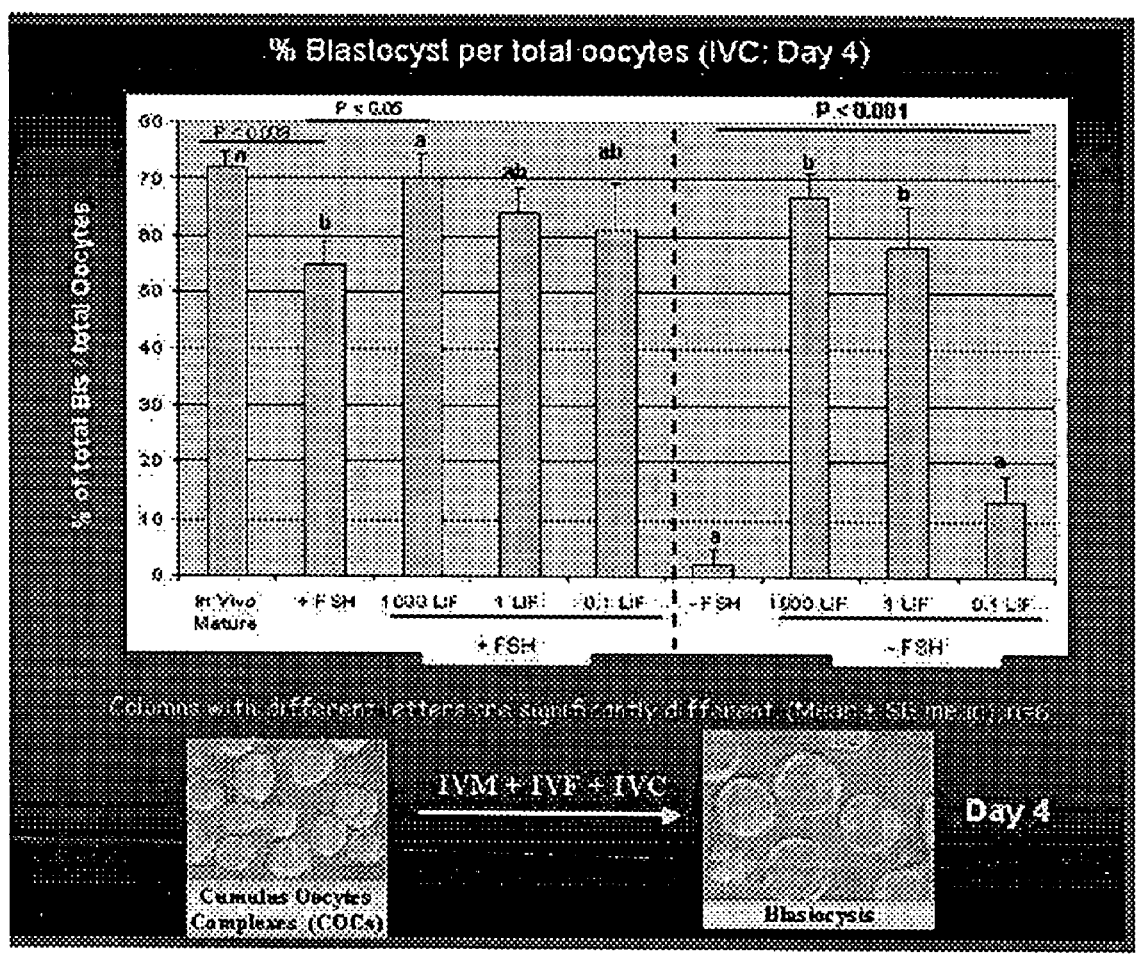
FIG. 14 demonstrates the effect of LIF on the total rate of blastocyst formation.
Figure 15:
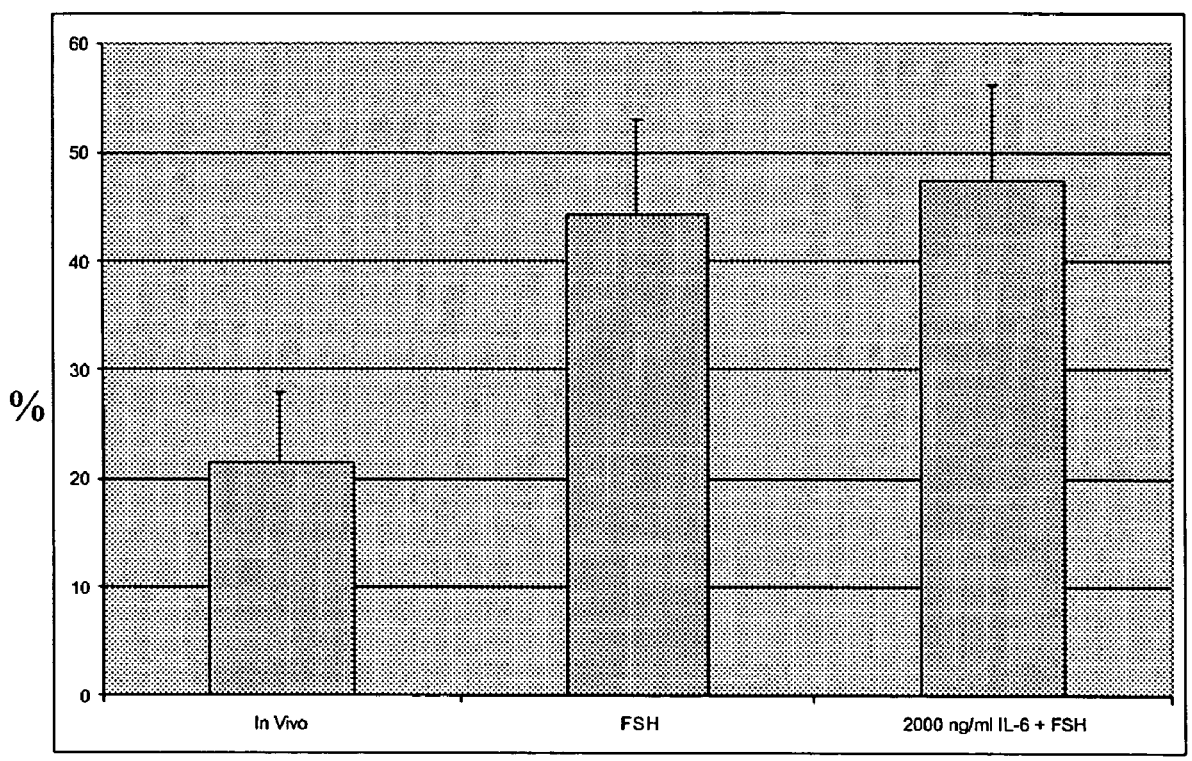
FIG. 15 demonstrates the effect of LIF on the total rate of blastocyst formation.

The rate of embryo development was measured at Day 4 based on the percentage of blastocysts. Similar to the results for the rate of in vitro fertilization, the (1000 ng/ml of LIF+FSH)—IVM group and in the in vivo-matured group showed a significant increase in blastocyst rate compared to the FSH-IVM group (FIG. 14). A similar increase in the blastocyst rate was seen with 2000 ng/ml of LIF+FSH (FIG. 15). In addition, LIF (1000 or 1 ng/ml) alone produced a significant increase in the blastocyst rate compared with the negative control (IVM medium without FSH) (FIG. 14).

Figure 16:
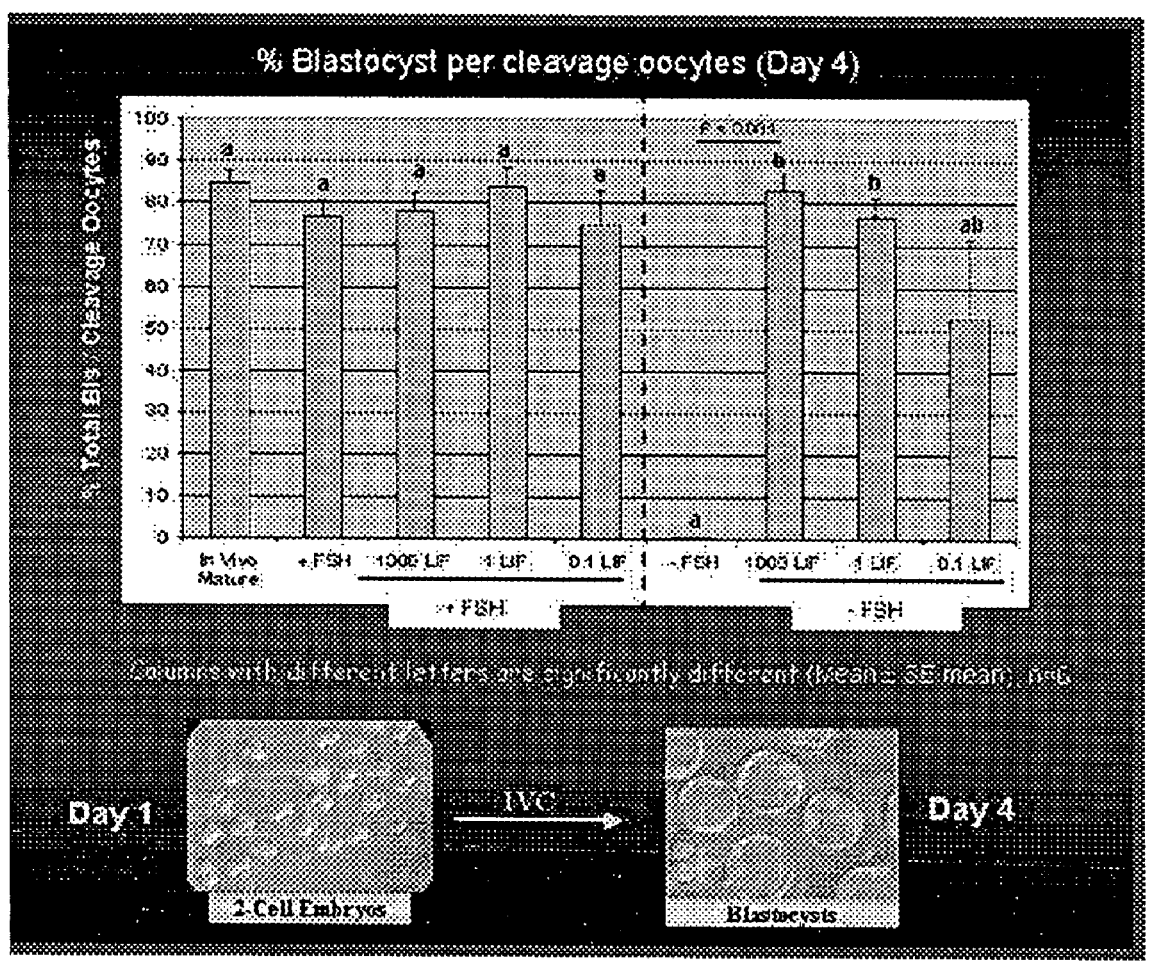
FIG. 16 demonstrates the effect of LIF on the rate of blastocyst formation from 2-cell embryos.

The rate of embryo development was also measured by determining the total number of blastocysts per 2-cell embryos. As shown in FIG. 16, approximately 80% of 2-cell embryos developed to blastocysts for all groups with oocytes matured in the presence of LIF and FSH, as well as in the in vivo-matured group. Groups with oocytes matured with LIF alone had similar results. There were no blastocysts in the negative control (-FSH). The rates were very variable for the groups with FSH and 0.1 ng/ml of LIF.

Figure 18:
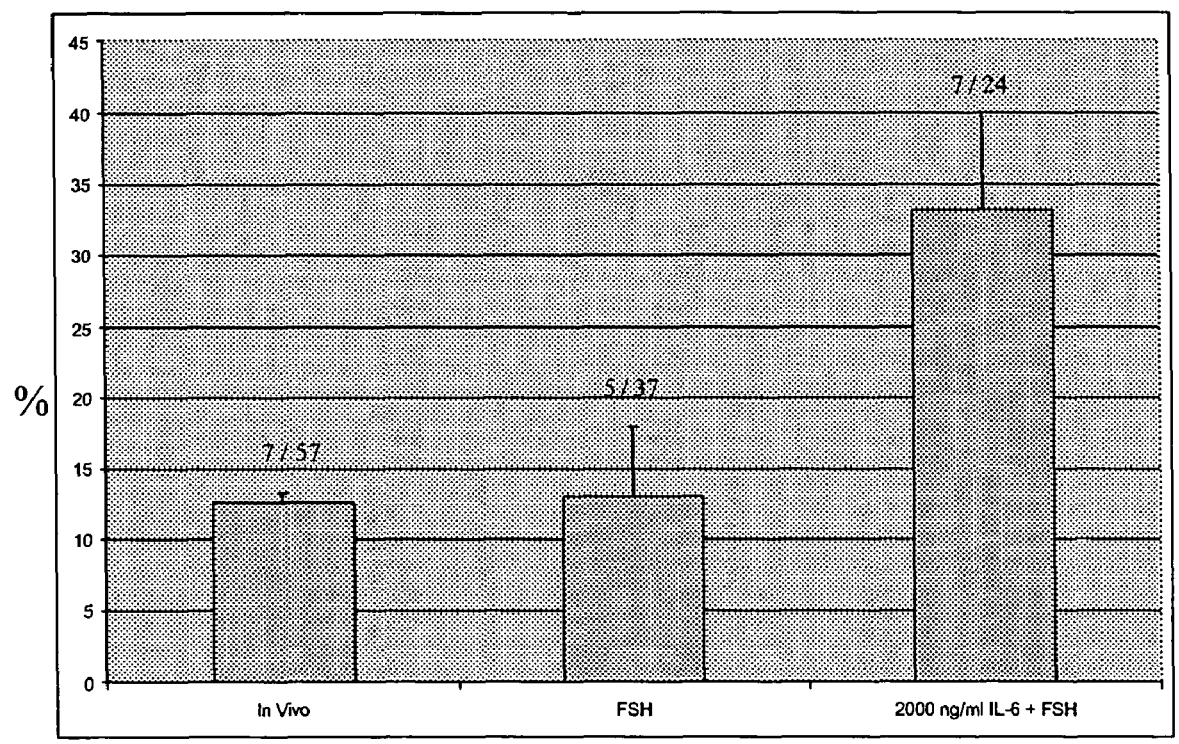
FIG. 18 demonstrates the effect of LIF on birth rates.

The birth rates for the different experimental groups were measured by surgically transferring Day 4 embryos to the uterine horn of 8-12 weeks-old CD1 2.5-days pseudopregnant females (Charles River). The embryos produced from oocytes in vitro-matured in medium with FSH and 1000 ng/ml of LIF had a higher birth rate ($0.05<p<0.07$) than the control group (FSH alone) and the same as the in vivo-matured group ($p>0.05$) (FIG. 17). A similar increase in the birth rate was seen with 2000 ng/ml of LIF+FSH (FIG. 18). In addition, the pregnancy rate was higher with FSH+1000 ng/ml LIF was slightly higher (FIG. 17).

The increase in fertilization rate, blastocyst rate and birth rate indicate that the addition of LIF to a standard mouse IVM medium increases oocyte quality.

The invention claimed is:

1. A method for the in vitro maturation of an isolated oocyte, comprising incubating said isolated oocyte in a physiologically acceptable medium comprising an IL-6-type cytokine, wherein said isolated oocyte is an immature cumulus-intact oocyte retrieved from an ovarian follicle of a female and whereby maturation of said immature oocyte is induced.

2. The method of claim 1 wherein the oocyte is at the stage of an early antral or antral follicle when retrieved from a female.

3. The method of claim 1 wherein the IL-6-type cytokine binds to a receptor selected from the group consisting of LIFR-gp130 heterodimers, OSMR-gp130 heterodimers, and gp130 homodimers.

4. The method of claim 1 wherein the IL-6-type cytokine does not bind to a receptor selected from the group consisting of IL-11Rα and CNTFRα.

5. The method of claim 1 wherein the IL-6-type cytokine is LIF.

6. The method of claim 1 wherein the IL-6-type cytokine is CT-1.

7. The method of claim 1 wherein the IL-6-type cytokine is IL-6.

8. The method of claim 1 wherein the IL-6-type cytokine is sIL-6Rα.

9. The method of claim 1 wherein the IL-6-type cytokine is IL-6/sIL-6Rα.

10. The method of claim 1 wherein the medium further comprises FSH, hCG, or a combination thereof.

11. The method of claim 1 wherein the medium does not comprise FSH, hCG, or a combination thereof.

* * * * *